United States Patent
Chow et al.

(10) Patent No.: US 10,160,803 B2
(45) Date of Patent: Dec. 25, 2018

(54) ANGIOPOIETIN-RELATED PROTEIN 4 (CANGPTL4) AS A DIAGNOSTIC BIOMARKER FOR ACUTE LUNG DAMAGE

(71) Applicants: National University of Singapore, Singapore (SG); Nanyang Technological University, Singapore (SG)

(72) Inventors: Vincent Tak Kwong Chow, Singapore (SG); Nguan Soon Tan, Singapore (SG); Liang Li, Singapore (SG); Ming Jie Tan, Singapore (SG); Han Chung Kelvin Chong, Singapore (SG)

(73) Assignees: National University of Singapore, Singapore (SG); Nanyang Technological University, Singapore (SG)

( * ) Notice: Subject to any disclaimer, the term of this patent is extended or adjusted under 35 U.S.C. 154(b) by 0 days.

(21) Appl. No.: 14/763,423

(22) PCT Filed: Jan. 23, 2014

(86) PCT No.: PCT/SG2014/000029
§ 371 (c)(1),
(2) Date: Jul. 24, 2015

(87) PCT Pub. No.: WO2014/116184
PCT Pub. Date: Jul. 31, 2014

(65) Prior Publication Data
US 2015/0368331 A1   Dec. 24, 2015

(30) Foreign Application Priority Data

Jan. 25, 2015 (GB) .................................. 1301313.1

(51) Int. Cl.
*G01N 33/53* (2006.01)
*A61K 39/395* (2006.01)
(Continued)

(52) U.S. Cl.
CPC .......... *C07K 16/22* (2013.01); *A61K 49/0008* (2013.01); *C12Q 1/6883* (2013.01);
(Continued)

(58) Field of Classification Search
None
See application file for complete search history.

(56) References Cited

U.S. PATENT DOCUMENTS 7,655,762 B2 *  2/2010  Lee ...................... C07K 14/515
8,092,796 B2    1/2012  Lee et al.
(Continued)

FOREIGN PATENT DOCUMENTS

WO   WO 2006/074228   7/2006
WO   WO 2011/046515   4/2011
(Continued)

OTHER PUBLICATIONS

Lei et al., Proteolytic processing of antgiopoeitin-like protein 4 by proprotein convertases modulates its inhibitory effects on lipoprotein lipase activity, J. Biol. Chem. 286(18):15747-15756, May 6, 2011.*
(Continued)

*Primary Examiner* — Claire Kaufman
(74) *Attorney, Agent, or Firm* — Klarquist Sparkman, LLP

(57) ABSTRACT

The invention relates to the C-terminal fragment of angiopoietin-related protein 4 [cAngptl4] as a diagnostic marker for viral and bacterial pneumonia; anti-angiopoietin-related protein 4 therapeutic antibodies, and the use of
(Continued)

anti-angiopoietin-related protein 4 antibodies in the treatment of viral and bacterial pneumonia.

7 Claims, 17 Drawing Sheets

Specification includes a Sequence Listing.

(51) Int. Cl.
    *A61K 45/00* (2006.01)
    *C07K 16/22* (2006.01)
    *G01N 33/569* (2006.01)
    *G01N 33/68* (2006.01)
    *C12Q 1/6883* (2018.01)
    *A61K 49/00* (2006.01)
    *G01N 33/74* (2006.01)
    *G06F 19/12* (2011.01)
    *A61K 39/00* (2006.01)

(52) U.S. Cl.
    CPC ....... *G01N 33/56911* (2013.01); *G01N 33/68* (2013.01); *G01N 33/74* (2013.01); *G06F 19/12* (2013.01); *A61K 2039/505* (2013.01); *C07K 2317/21* (2013.01); *C07K 2317/24* (2013.01); *C07K 2317/34* (2013.01); *C12Q 2600/106* (2013.01); *C12Q 2600/118* (2013.01); *C12Q 2600/158* (2013.01); *G01N 2333/515* (2013.01); *G01N 2500/04* (2013.01); *G01N 2500/20* (2013.01); *G01N 2800/50* (2013.01); *G01N 2800/52* (2013.01); *G01N 2800/70* (2013.01); *G01N 2800/7095* (2013.01)

(56) References Cited

U.S. PATENT DOCUMENTS

2006/0093607 A1    5/2006    Gerber et al.
2011/0159015 A1*    6/2011    Sleeman ............ A61K 39/3955
2011/0311524 A1    12/2011    Gerber et al.

FOREIGN PATENT DOCUMENTS

WO    WO 2013/022406    2/2013
WO    WO 2014/027959    2/2014

OTHER PUBLICATIONS

NIH, National Heart, Lung, and Blood Institute, What is Asthma? URL: <<https://www.nhlbi.nih.gov/health/health-topics/topics/asthma>> [Retrieved online Feb. 16, 2017] updated Aug. 4, 2014.*
NIH, National Cancer Institute, NCIthesaurus, version 17.01e, released Jan. 30, 2016, Code C25263 and C18959. URL:<<https://ncit.nci.nih.gov/ncitbrowser/pages/home.jsf?version=17.01e>>, [Retrieved online Feb. 17, 2017] released Jan. 30, 2016.*
Johnson et al., Acute lung injury: epidemiology, pathology, and treatment, (J. Aerosol. Med. Pulm. Drug Deliv. 23(4):243-252, 2010.*
Yang et al., Attenuation of acute lung inflammation and injury by whole body cooling in a rat heatstroke model. J. Biomed. Biotechnol. [serial on the Internet: URL<http://dx.doi.org/10.1155/2009/768086>]. vol. 2009 [accessed Nov. 28, 2017], Article ID: 768086, 2009.*
Ranieri et al., Acute respiratory distress syndrome:The Berlin definition, JAMA 307(23):2526-2533, 2012.*
Chamberland et al., A comparison of two sets of microarray experiments to define allergic asthma expression pattern, Exp. Lung Res. 35 :399-410, 2009.*
Han et al., The acute respiratory distress syndrome: from mechanism to translation, J. Immunol. 194:855-860, 2015.*
Moldoveanu et al., Inflammatory mechanisms in the lung, J. Inflamm. Res., 2:1-11, 2009.*
Lee, J., Cryptogenic organizing pneumonia, Merck Manual. [retrieved online on Mar. 2, 2018] URL:< https://www.merckmanuals.com/professional/pulmonary-disorders/interstitial-lung-diseases/cryptogenic-organizing-pneumonia>, 2016.*
Akaike, et al. "Pathogenesis of influenza virus-induced pneumonia: involvement of both nitric oxide and oxygen radicals." *Proceedings of the National Academy of Sciences* 93, No. 6 (1996): 2448-2453.
Buchweitz, et al. "Time-dependent airway epithelial and inflammatory cell responses induced by influenza virus A/PR/8/34 in C57BL/6 mice." *Toxicologic Pathology* 35, No. 3 (2007): 424-435.
Enzo Life Sciences, "ANGPTLs [Angiopoietin-like proteins]," published Nov. 1, 2009 (online Product Flyer (International Edition)) Available online at: http://www.enzolifesciences.com/fileadmin/files/minicatalog/flyer_angptls_np__final.pdf. Last accessed Jul. 6, 2015, 6 pages.
Huang, et al. "ANGPTL4 modulates vascular junction integrity by integrin signaling and disruption of intercellular VE-cadherin and claudin-5 clusters." *Blood* 118, No. 14 (2011): 3990-4002.
Lichtenstein, et al. "Angptl4 protects against severe proinflammatory effects of saturated fat by inhibiting fatty acid uptake into mesenteric lymph node macrophages." *Cell Metabolism* 12, No. 6 (2010): 580-592.
Pal, et al. "Angiopoietin-like 4 regulates epidermal differentiation," *PLoS ONE* 6, No. 9 (2011): e25377.
Yin, et al. "Genetic variation in ANGPTL4 provides insights into protein processing and function." *Journal of Biological Chemistry* 284, No. 19 (2009): 13213-13222.
Zheng, et al. "Regeneration of alveolar type I and II cells from Scgb1a1-expressing cells following severe pulmonary damage induced by bleomycin and influenza." *PLoS ONE* 7, No. 10 (2012): e48451.
Zhu, et at. "Angiopoietin-like 4 protein elevates the prosurvival intracellular O 2—: H 2 O 2 ratio and confers anoikis resistance to tumors." *Cancer Cell* 19, No. 3 (2011): 401-415.
Zhu, et al. "Angiopoietin-like 4: a decade of research." *Bioscience Reports* 32, No. 3 (2012): 211-219.
Li, et al. "Angiopoietin-like 4 increases pulmonary tissue leakiness and damage during influenza pneumonia." *Cell Reports* 10, No. 5 (2015): 654-663.

* cited by examiner

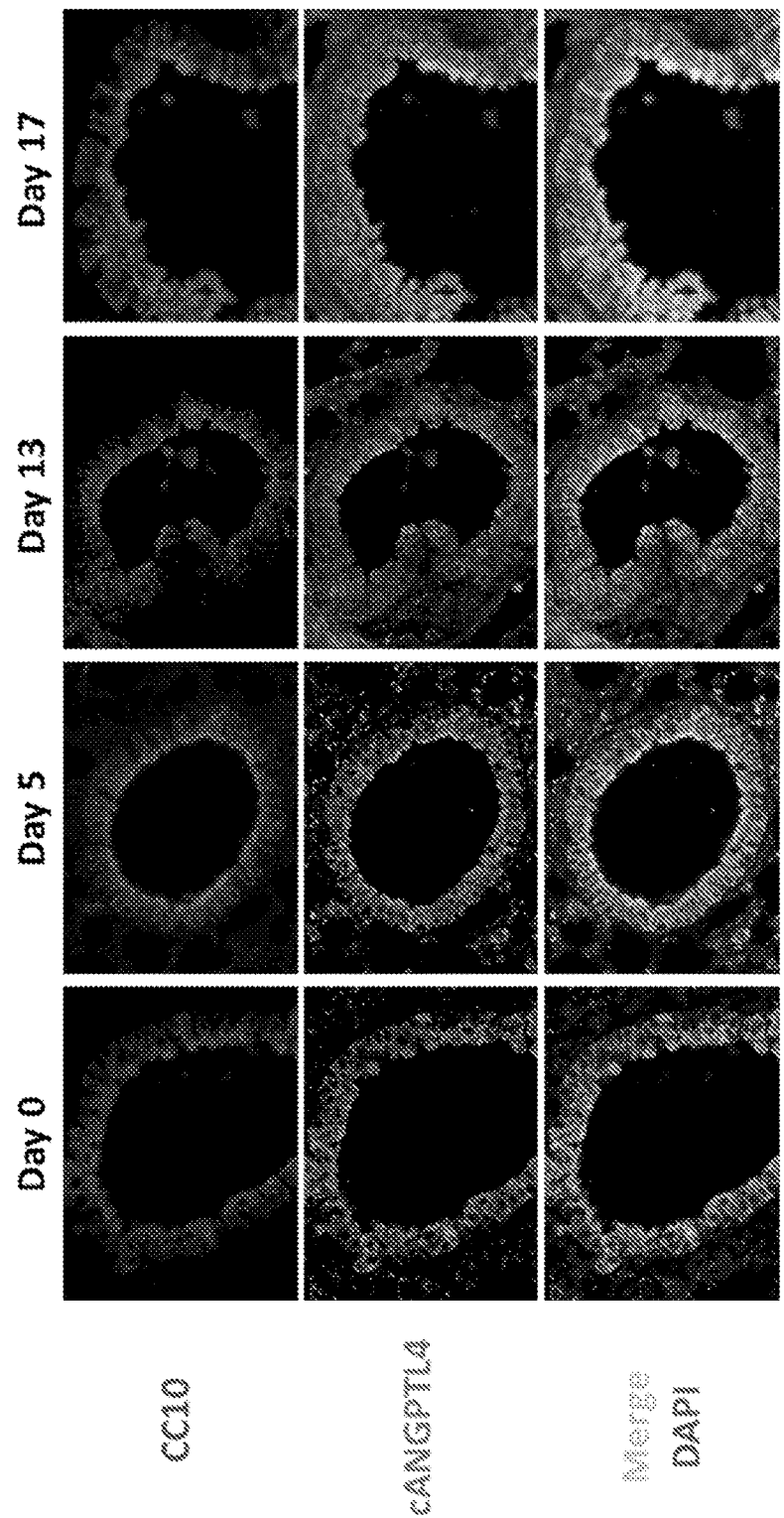

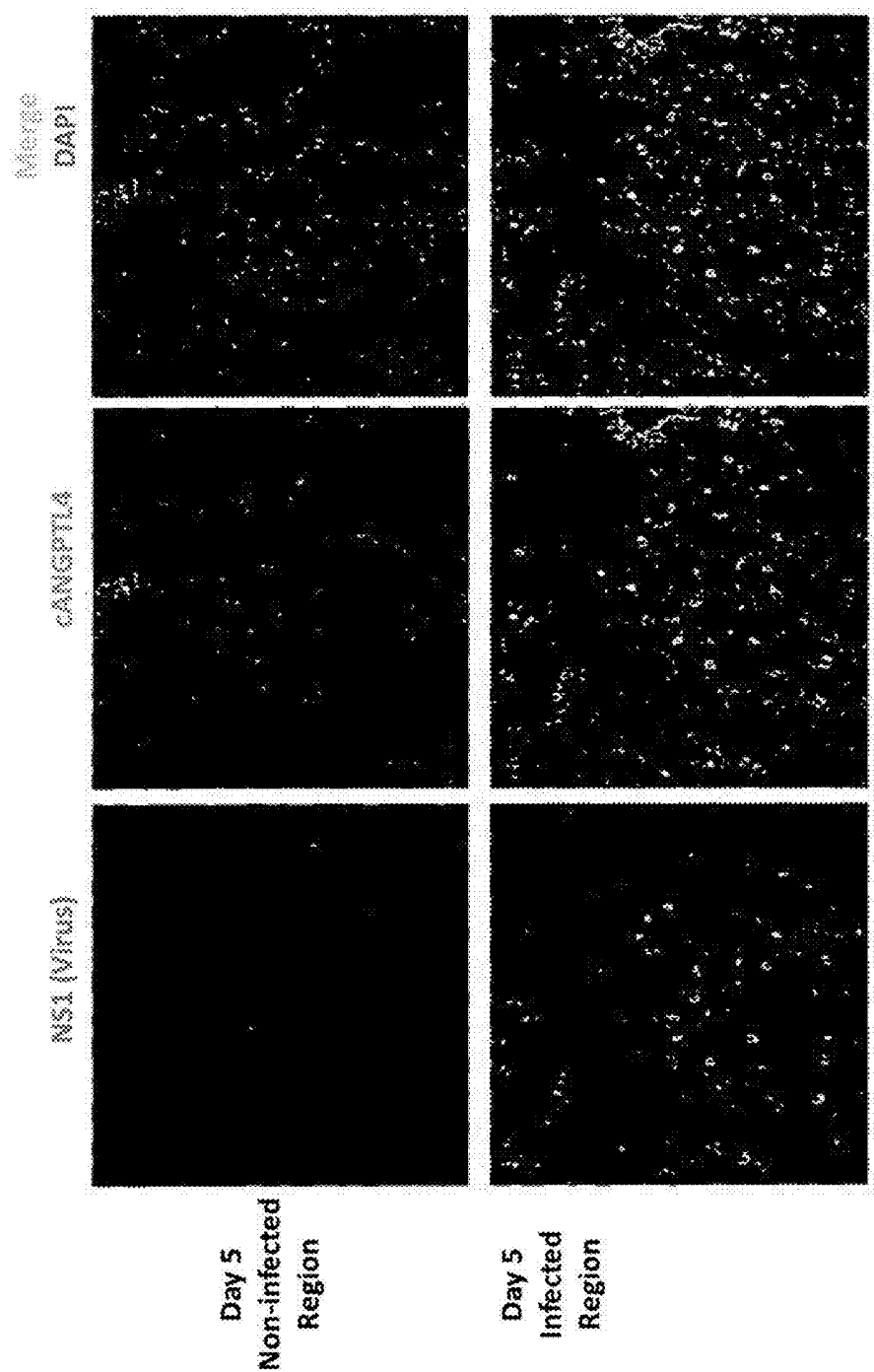

Mouse BALF cANGPTL4 cANGPTL4 Staining

SEQUENCE LISTING

```
<160> NUMBER OF SEQ ID NOS: 26

<210> SEQ ID NO 1
<211> LENGTH: 222
<212> TYPE: PRT
<213> ORGANISM: Homo sapiens

<400> SEQUENCE: 1

Pro Arg Asp Cys Gln Glu Leu Phe Gln Val Gly Glu Arg Gln Ser Gly
1               5                   10                  15
```

```
Leu Phe Glu Ile Gln Pro Gln Gly Ser Pro Pro Phe Leu Val Asn Cys
            20                  25                  30

Lys Met Thr Ser Asp Gly Gly Trp Thr Val Ile Gln Arg Arg His Asp
        35                  40                  45

Gly Ser Val Asp Phe Asn Arg Pro Trp Glu Ala Tyr Lys Ala Gly Phe
    50                  55                  60

Gly Asp Pro His Gly Glu Phe Trp Leu Gly Leu Glu Lys Val His Ser
65                  70                  75                  80

Ile Thr Gly Asp Arg Asn Ser Arg Leu Ala Val Gln Leu Arg Asp Trp
                85                  90                  95

Asp Gly Asn Ala Glu Leu Leu Gln Phe Ser Val His Leu Gly Gly Glu
            100                 105                 110

Asp Thr Ala Tyr Ser Leu Gln Leu Thr Ala Pro Val Ala Gly Gln Leu
        115                 120                 125

Gly Ala Thr Thr Val Pro Pro Ser Gly Leu Ser Val Pro Phe Ser Thr
    130                 135                 140

Trp Asp Gln Asp His Asp Leu Arg Arg Asp Lys Asn Cys Ala Lys Ser
145                 150                 155                 160

Leu Ser Gly Gly Trp Trp Phe Gly Thr Cys Ser His Ser Asn Leu Asn
                165                 170                 175

Gly Gln Tyr Phe Arg Ser Ile Pro Gln Gln Arg Gln Lys Leu Lys Lys
            180                 185                 190

Gly Ile Phe Trp Lys Thr Trp Arg Gly Arg Tyr Tyr Pro Leu Gln Ala
        195                 200                 205

Thr Thr Met Leu Ile Gln Pro Met Ala Ala Glu Ala Ala Ser
    210                 215                 220

<210> SEQ ID NO 2
<211> LENGTH: 221
<212> TYPE: PRT
<213> ORGANISM: Mus musculus

<400> SEQUENCE: 2

Arg Asp Cys Gln Glu Leu Phe Gln Gly Glu Arg His Ser Gly Leu
1               5                   10                  15

Phe Gln Ile Gln Pro Leu Gly Ser Pro Pro Phe Leu Val Asn Cys Glu
            20                  25                  30

Met Thr Ser Asp Gly Gly Trp Thr Val Ile Gln Arg Arg Leu Asn Gly
        35                  40                  45

Ser Val Asp Phe Asn Gln Ser Trp Glu Ala Tyr Lys Asp Gly Phe Gly
    50                  55                  60

Asp Pro Gln Gly Glu Phe Trp Leu Gly Leu Glu Lys Met His Ser Ile
65                  70                  75                  80

Thr Gly Asn Arg Gly Ser Gln Leu Ala Val Gln Leu Gln Asp Trp Asp
                85                  90                  95

Gly Asn Ala Lys Leu Leu Gln Phe Pro Ile His Leu Gly Gly Glu Asp
            100                 105                 110

Thr Ala Tyr Ser Leu Gln Leu Thr Glu Pro Thr Ala Asn Glu Leu Gly
        115                 120                 125

Ala Thr Asn Val Ser Pro Asn Gly Leu Ser Leu Pro Phe Ser Thr Trp
    130                 135                 140

Asp Gln Asp His Asp Leu Arg Gly Asp Leu Asn Cys Ala Lys Ser Leu
145                 150                 155                 160

Ser Gly Gly Trp Trp Phe Gly Thr Cys Ser His Ser Asn Leu Asn Gly
```

```
                        165                 170                 175
Gln Tyr Phe His Ser Ile Pro Arg Gln Arg Gln Glu Arg Lys Lys Gly
            180                 185                 190

Ile Phe Trp Lys Thr Trp Lys Gly Arg Tyr Tyr Pro Leu Gln Ala Thr
        195                 200                 205

Thr Leu Leu Ile Gln Pro Met Glu Ala Thr Ala Ala Ser
    210                 215                 220

<210> SEQ ID NO 3
<211> LENGTH: 15
<212> TYPE: PRT
<213> ORGANISM: Homo sapiens

<400> SEQUENCE: 3

Gln Tyr Phe Arg Ser Ile Pro Gln Gln Arg Gln Lys Leu Lys Lys
1               5                   10                  15

<210> SEQ ID NO 4
<211> LENGTH: 15
<212> TYPE: PRT
<213> ORGANISM: Mus musculus

<400> SEQUENCE: 4

Gln Tyr Phe His Ser Ile Pro Arg Gln Arg Gln Glu Arg Lys Lys
1               5                   10                  15

<210> SEQ ID NO 5
<211> LENGTH: 669
<212> TYPE: DNA
<213> ORGANISM: Homo sapiens

<400> SEQUENCE: 5 cccaggggatt gccaggagct gttccaggtt ggggagaggc agagtggact atttgaaatc    60
cagcctcagg ggtctccgcc attttttggtg aactgcaaga tgacctcaga tggaggctgg   120
acagtaattc agaggcgcca cgatggctca gtggacttca accggccctg ggaagcctac   180 aaggcgggt ttggggatcc ccacggcgag ttctggctgg gtctggagaa ggtgcatagc   240
atcacggggg accgcaacag ccgcctggcc gtgcagctgc gggactggga tggcaacgcc   300
gagttgctgc agttctccgt gcacctgggt ggcgaggaca cggcctatag cctgcagctc   360
actgcacccg tggccggcca gctgggcgcc accaccgtcc cacccagcgg cctctccgta   420
cccttctcca cttgggacca ggatcacgac ctccgcaggg acaagaactg cgccaagagc   480
ctctctggag gctggtggtt tggcacctgc agcattccaa acctcaacgg ccagtacttc   540
cgctccatcc cacagcagcg gcagaagctt aagaagggaa tcttctggaa gacctggcgg   600
ggccgctact acccgctgca ggccaccacc atgttgatcc agcccatggc agcagaggca   660
gcctcctag                                                            669

<210> SEQ ID NO 6
<211> LENGTH: 666
<212> TYPE: DNA
<213> ORGANISM: Mus musculus

<400> SEQUENCE: 6
cgggactgcc aggaactctt ccaagaaggg agcggcaca gtggacttt ccagatccag    60 cctctgggt ctccaccatt tttggtcaac tgtgagatga cttcagatgg aggctggaca   120
gtgattcaga gacgcctgaa cggctctgtg gacttcaacc agtcctggga agcctacaag   180
```

```
gatggcttcg gagatcccca aggcgagttc tggctgggcc tggaaaagat gcacagcatc    240
acagggaacc gaggaagcca attggctgtg cagctccagg actgggatgg caatgccaaa    300
ttgctccaat ttcccatcca tttgggggt gaggacacag cctacagcct gcagctcact     360
gagcccacgg ccaatgagct gggtgccacc aatgtttccc ccaatggcct ttccctgccc    420
ttctctactt gggaccaaga ccatgacctc cgtggggacc ttaactgtgc caagagcctc    480
tctggtggct ggtggtttgg tacctgtagc cattccaatc tcaatggaca atacttccac    540
tctatcccac ggcaacggca ggagcgtaaa aagggtatct tctggaaaac atggaagggc    600
cgctactatc tctgcaggc taccaccctg ctgatccagc ccatggaggc tacagcagcc     660
tcttag                                                               666

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
tggtttggca cctgcagcca ttc                                             23

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
tgctgccatg ggctggatca ac                                              22

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
tccaacgcca cccacttac                                                  19

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
tgaagtcatc tcacagttga cca                                             23

<210> SEQ ID NO 11
<211> LENGTH: 336
<212> TYPE: DNA
<213> ORGANISM: Homo sapiens

<400> SEQUENCE: 11
gacatcgagc tcactcagtc tccagcttct ttggctgtgt ctctagggca gagggccacc     60
atctcctgca aggccagcca aagtgttgat tatgatggtg atagttattt gaactggttc    120
caacagaaac cgggacagcc acccaaactc ctcatctata ctgcatccaa tctagaatct    180
```

```
ggaatcccag ccaggtttag tggcagtggg tctgggacag acttcaccct caacatccat      240
cctgtggagg aggaggatgc tgcaacctat tactgtcagc agagtaatga ggatccgtgg      300
acgttcggtg gaggcaccaa gttggaaata aaacgg                                336
```

<210> SEQ ID NO 12
<211> LENGTH: 354
<212> TYPE: DNA
<213> ORGANISM: Homo sapiens

<400> SEQUENCE: 12

```
caggtgcaac tgcaggagtc tggccctggg atattgaagc cctcacagac cctcagtctg       60
acttgttctt tctctgggtt ttcactgagc acttctggta tgggtgtagg ctggattcgt      120
cagccttcag ggaagggtct ggagtggctg gcacacattt ggtgggatga tgataagtac      180
tataacccat ccctgaagag ccagctcaca atctccaagg atacctccag aaaccaggta      240
ttcctcaaga tcatcagtgt ggacactgca gatactgcca cttactactg tgctcgaaaa      300
gactacggta gtagttacga ctactggggc caagggacca cggtcaccgt ctcc            354
```

<210> SEQ ID NO 13
<211> LENGTH: 112
<212> TYPE: PRT
<213> ORGANISM: Homo sapiems

<400> SEQUENCE: 13

Asp Ile Glu Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Phe Gln Gln Lys Pro Gly Gln Pro Pro
        35                  40                  45

Lys Leu Leu Ile Tyr Thr Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys Arg
            100                 105                 110

<210> SEQ ID NO 14
<211> LENGTH: 118
<212> TYPE: PRT
<213> ORGANISM: Homo sapiens

<400> SEQUENCE: 14

Gln Val Gln Leu Gln Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

```
Phe Leu Lys Ile Ile Ser Val Asp Thr Ala Asp Thr Ala Thr Tyr Tyr
            85                  90                  95

Cys Ala Arg Lys Asp Tyr Gly Ser Ser Tyr Asp Tyr Trp Gly Gln Gly
            100                 105                 110

Thr Thr Val Thr Val Ser
        115

<210> SEQ ID NO 15
<211> LENGTH: 45
<212> TYPE: DNA
<213> ORGANISM: artificial sequence
<220> FEATURE:
<223> OTHER INFORMATION: Epitope

<400> SEQUENCE: 15
aaggccagcc aaagtgttga ttatgatggt gatagttatt tgaac                45

<210> SEQ ID NO 16
<211> LENGTH: 15
<212> TYPE: PRT
<213> ORGANISM: Artificial Sequence
<220> FEATURE:
<223> OTHER INFORMATION: Epitope

<400> SEQUENCE: 16

Lys Ala Ser Gln Ser Val Asp Tyr Asp Gly Asp Ser Tyr Leu Asn
1               5                   10                  15

<210> SEQ ID NO 17
<211> LENGTH: 21
<212> TYPE: DNA
<213> ORGANISM: Artificial Sequence
<220> FEATURE:
<223> OTHER INFORMATION: Epitope

<400> SEQUENCE: 17
actgcatcca atctagaatc t                                          21

<210> SEQ ID NO 18
<211> LENGTH: 7
<212> TYPE: PRT
<213> ORGANISM: Artificial Sequence
<220> FEATURE:
<223> OTHER INFORMATION: Epitope

<400> SEQUENCE: 18

Thr Ala Ser Asn Leu Glu Ser
1               5

<210> SEQ ID NO 19
<211> LENGTH: 24
<212> TYPE: DNA
<213> ORGANISM: Artificial Sequence
<220> FEATURE:
<223> OTHER INFORMATION: Epitope

<400> SEQUENCE: 19
cagcagagta atgaggatcc gtgg                                       24

<210> SEQ ID NO 20
<211> LENGTH: 8
<212> TYPE: PRT
<213> ORGANISM: Artificial Sequence
<220> FEATURE:
<223> OTHER INFORMATION: Epitope
```

<400> SEQUENCE: 20

Gln Gln Ser Asn Glu Asp Pro Trp
1               5

<210> SEQ ID NO 21
<211> LENGTH: 21
<212> TYPE: DNA
<213> ORGANISM: Artificial Sequence
<220> FEATURE:
<223> OTHER INFORMATION: Epitope

<400> SEQUENCE: 21
acttctggta tgggtgtagg c                                             21

<210> SEQ ID NO 22
<211> LENGTH: 7
<212> TYPE: PRT
<213> ORGANISM: Artificial Sequence
<220> FEATURE:
<223> OTHER INFORMATION: Epitope

<400> SEQUENCE: 22

Thr Ser Gly Met Gly Val Gly
1               5

<210> SEQ ID NO 23
<211> LENGTH: 45
<212> TYPE: DNA
<213> ORGANISM: Artificial Sequence
<220> FEATURE:
<223> OTHER INFORMATION: Epitope

<400> SEQUENCE: 23
cacatttggt gggatgatga taagtactat aacccatccc tgaag                   45

<210> SEQ ID NO 24
<211> LENGTH: 15
<212> TYPE: PRT
<213> ORGANISM: Artificial Sequence
<220> FEATURE:
<223> OTHER INFORMATION: Epitope

<400> SEQUENCE: 24

His Ile Trp Trp Asp Asp Asp Lys Tyr Tyr Asn Pro Ser Leu Lys
1               5                   10                  15

<210> SEQ ID NO 25
<211> LENGTH: 27
<212> TYPE: DNA
<213> ORGANISM: Artificial Sequence
<220> FEATURE:
<223> OTHER INFORMATION: Epitope

<400> SEQUENCE: 25
aaagactacg gtagtagtta cgactac                                       27

<210> SEQ ID NO 26
<211> LENGTH: 9
<212> TYPE: PRT
<213> ORGANISM: Artificial Sequence
<220> FEATURE:
<223> OTHER INFORMATION: Epitope

```
<400> SEQUENCE: 26

Lys Asp Tyr Gly Ser Ser Tyr Asp Tyr
1               5
```

ANGIOPOIETIN-RELATED PROTEIN 4 (CANGPTL4) AS A DIAGNOSTIC BIOMARKER FOR ACUTE LUNG DAMAGE

CROSS REFERENCE TO RELATED APPLICATIONS

This is the U.S. National Stage of International Application No. PCT/SG2014/000029, filed Jan. 23, 2014, which was published in English under PCT Article 21(2), which in turn claims the benefit of Great Britain Application No. 1301313.1, filed Jan. 25, 2013.

FIELD OF THE INVENTION

The invention relates to a C-terminal fragment of angiopoietin-related protein 4 [cAngptl4] as a diagnostic marker for viral and bacterial pneumonia, anti-angiopoietin-related protein 4 therapeutic antibodies, and the use of anti-c-angiopoietin-related protein 4 antibodies in the treatment of viral and bacterial pneumonia.

BACKGROUND TO THE INVENTION

Lower respiratory tract infections are according to the World Health Organisation (WHO) the leading cause of deaths in lower and middle income countries and the third cause of death in the world. Lower respiratory tract infections are prevalent in young children under five and the elderly, and can lead to complications such as emphysema, lung abscess, bronchiolitis obliterans, acute respiratory distress syndrome and sepsis putting a huge financial burden on the health system worldwide.

There are a number of acute and chronic infections that can affect the lower respiratory tract. The two most common infections are bronchitis and pneumonia. Bronchitis is typically caused by viruses, and to a lesser extent by bacteria that infect the epithelium of the bronchi causing inflammation. Pneumonia is described as inflammation of the lung alveoli, leading to chest pain, fever and difficulty breathing. Pneumonia is typically caused by bacteria and viruses and can also be caused by fungi and other microorganism. The bacterium *Streptococcus pneumonia*, is one of the most common causes of pneumonia, and others include *Haemophillus influenza, Chlamydophila pneumonia* or *Mycoplasma pneumonia*. Around one third of infections are caused by viruses as for example rhinoviruses, coronaviruses, influenza virus, adenovirus or respiratory syncytial virus.

Bronchitis and pneumonia are typically diagnosed using various tests including physical examination, X-rays, sputum culture or pulmonary function tests. The treatment of bronchitis and pneumonia is depended on the causative agent. Bacteria can be widely treated with antibiotic. However, inappropriate use of antibiotics has resulted in strains with multiple antibiotic resistances. Viral Pneumonia can be treated with antiviral medication. Nevertheless, the effectiveness of such medication is dependent on the virus type and on the general health of the patient. Moreover, the use of antivirals can be problematic as they can cause severe side effects. Treatment of damaged lung tissue includes the use of anti-inflammatory agents, which can also be difficult as they are commonly known to suppress immune function which again can have serious consequences leading to secondary infections.

The angiopoietin-like proteins (ANGPTL 1-7) belong to a superfamily of angiogenic-regulating, secreted proteins that bear the highest similarity to members of the angiopoietin (Ang) family. Angptl4 has been recognized as a central player in various aspects of energy homoeostasis, and was found to be involved in wound healing, modulation of vascular permeability and the regulation of reactive oxygen species promoting tumourigenesis. None of the ANGPTL proteins binds to TIE 1/2 tyrosine kinase receptors, suggesting that they may exert distinct functions from the other ANG-proteins.

Like other members of this family, Angptl4 contains a secretory signal peptide, a predicted N-terminal coiled-coil quaternary structure and a large, C-terminal fibrinogen-like domain. The N-terminal region of Angptl4 (nAngptl4) is responsible for assembly into oligomeric structures which is important for its function as a lipoprotein lipase inhibitor. Full-length Angptl4 undergoes proteolytic processing at a linker region, thereby releasing nAngptl4 and the monomeric C-terminal portion of Angptl4 (cAngptl4). The cAngptl4 interacts with integrins β1/5, VE-cadherin and claudin-5 to stimulate intracellular signalling that aid wound healing. Expression of ANGPTL4 can be induced by numerous stimuli, such as glucocorticoid, TGFβ, nuclear hormone receptor PPARs and HIF-alpha.

Increased levels of Angptl4 have been measured in many human tumours, for example, renal carcinomas, oral tongue squamous cell carcinomas and human gastric cancers, and expression increased as tumours progress from benign to metastatic states. Studies suggest an involvement of Angptl4 in tumour growth and play a role through lymphovascular invasion. Patent application US2011311524 and US2006093607 discloses Angptl4 inhibitors and modulators for the treatment of cancer and other pathological conditions.

The use of antibodies as a tool for therapy is gaining increased popularity. Antibodies can be used to prevent tumour growth or to treat hormone imbalance by blocking specific receptors. Antibodies are also used in radioimmuno therapy to direct the radioactive compound to its specific target preserving healthy tissue. Humanized monoclonal antibodies are being used for the treatment of autoimmune diseases as different types of arthritis or Crohn's disease by blocking Tumour Necrosis Factor-alpha, a cytokine involved in systemic inflammation.

The authors have surprisingly found that cAngptl4 levels are significantly increased in damaged lung tissue following a bacterial or viral pneumonia infection. Moreover, anti-cAngptl4 monoclonal antibodies are shown to facilitate repair of damaged lung tissue.

The present disclosure relates to the use of cAngptl4 as diagnostic marker to diagnose acute lung damage caused by viral or bacterial infection and including cAngptl4 specific antibodies and their use in the treatment of viral or bacterial pneumonia.

SUMMARY OF INVENTION

According to an aspect of the invention there is provided a binding agent comprising a ligand that binds the carboxyl-terminal fragment of angiopoietin-related protein 4, or an amino acid sequence variant that retains the function of a polypeptide having the activity associated with angiopoietin-related protein 4, for use in the treatment of a microbial infection.

In a preferred embodiment of the invention said ligand binds an amino acid sequence as set forth in SEQ ID NO: 1 or SEQ ID NO: 2.

In a preferred embodiment of the invention said sequence variant that retains the function of a polypeptide having the activity associated with angiopoietin-related protein 4 is a polymorphic variant of said amino acid sequence.

In an alternative preferred embodiment of the invention said ligand binds an amino acid sequence: QYFRSIPQQRQKLKK [SEQ ID NO: 3].

In a further alternative preferred embodiment of the invention said ligand binds an amino acid sequence: QYFHSIPRQRQERKK [SEQ ID NO: 4].

In a preferred embodiment of the invention said ligand is an antibody or an antibody fragment comprising active binding part of said antibody.

In a preferred embodiment of the invention said antibody is a monoclonal antibody or a binding fragment derived from a monoclonal antibody.

Preferably said antibody is a chimeric antibody.

In an alternative preferred embodiment of the invention said antibody is a humanized or human antibody.

In a preferred embodiment of the invention there is provided an antibody, or active binding fragment thereof, wherein said antibody or fragment is selected from the group consisting of:
i) an antibody comprising or consisting of an amino acid sequence as represented in SED ID NO: 13 and/or SEQ ID NO: 14;
ii) an antibody comprising light chain complementarity determining regions including the amino acid sequences KASQSVDYDGDSYLN [SEQ ID NO: 16] and TASNLES [SEQ ID NO: 18] and QQSNEDPW [SEQ ID NO: 20] and/or an antibody comprising heavy chain complementarity determining regions including the amino acid sequences TSGMGVG [SEQ ID NO: 22] and HIWWDDDKYYNPSLK [SEQ ID NO: 24] and KDYGSSYDY [SEQ ID NO: 26];
iii) an antibody that binds a polypeptide comprising an amino acid sequence as set forth in SEQ ID NO: 1, SEQ ID NO: 2, SEQ ID NO: 3 or SEQ ID NO: 4;
iv) an antibody that competes with an antibody as represented by the amino acid sequences in i) or ii) above for binding to a polypeptide as defined in iii) above;
v) a fragment comprising or consisting of the amino acid sequence selected from the group consisting of KASQSVDYDGDSYLN [SEQ ID NO: 16] and TASNLES [SEQ ID NO: 18] and QQSNEDPW [SEQ ID NO: 20] and/or an antibody comprising heavy chain complementarity determining regions including the amino acid sequences TSGMGVG [SEQ ID NO: 22] and HIWWDDDKYYNPSLK [SEQ ID NO: 24] and KDYGSSYDY [SEQ ID NO: 26].

In a preferred embodiment of the invention said ligand is antagonist and binds a polypeptide comprising or consisting of the amino acid sequence set forth in SEQ ID NO: 1 or 2 to inhibit activity of angiopoietin-related protein 4.

More particularly said antagonist binds the amino acid sequence set forth in SEQ ID NO: 3 or 4.

In a preferred embodiment of the invention said microbial infection is associated with lung inflammation.

In a preferred embodiment of the invention said lung inflammation is pneumonia.

In an alternative preferred embodiment of the invention said lung inflammation is bronchitis.

In a preferred embodiment of the invention said microbial infection is caused by a bacterial pathogen.

In a preferred embodiment said bacterial pathogen is selected from the group consisting of *Streptococcus pneumonia*, *Haemophilus influenza*, *Chlamydophila pneumonia*, *Mycoplasma pneumonia*, *Moraxella catarrhalis*, *Legionella pneumophila*, *Chlamydia psittaci*, *Coxiella burnetti*, *Pseudomonas aeruginosa* and *Staphylococcus aureus*.

In an alternative preferred embodiment of the invention said microbial infection is caused by a viral pathogen.

In a preferred embodiment said viral pathogen is selected from the group consisting of rhinovirus, influenza virus, respiratory syncytial virus (RSV), adenovirus, parainfluenza, Herpes simplex, hantaviruses and coronavirus.

In further alternative embodiment of the invention said microbial infection is caused by a fungal pathogen.

In a preferred embodiment said fungal pathogen is selected from the group consisting of: *Histoplasma capsulatum*, *Blastomyces dermatitidis*, *Cryptococcus neoformans*, *Pneumocystis jiroveci*, and *Coccidioides immitis*.

In a preferred embodiment of the invention said ligand is adapted to be delivered as an aerosol.

According to a further aspect of the invention there is provided a pharmaceutical composition comprising a ligand that binds a polypeptide comprising a carboxyl-terminal fragment of angiopoietin-related protein 4, or an amino acid sequence variant that retains the function of a polypeptide having the activity associated with angiopoietin-related protein 4, including a pharmaceutical excipient and/or carrier.

In a preferred embodiment of the invention of the invention said polypeptide comprises or consists of the amino acid sequence set forth in SEQ ID NO: 1 or 2.

Preferably said polypeptide comprises the amino acid sequence set forth in SEQ ID NO: 3 or 4.

In a preferred embodiment of the invention said pharmaceutical composition is formulated as an aerosol.

According to a further aspect of the invention there is provided an inhaler comprising a pharmaceutical composition according to the invention.

According to a further aspect of the invention there is provided a diagnostic method for determining if a subject has or is predisposed to acute inflammation of the lung in response to a microbial infection comprising:

i) providing an isolated biological sample to be tested and preparing cDNA;

ii) forming a preparation comprising said cDNA and an oligonucleotide primer pair adapted to anneal to a nucleic acid molecule comprising a nucleotide sequence as set forth in SEQ ID NO: 5 or 6; a thermostable DNA polymerase, deoxynucleotide triphosphates and co-factors;

iii) providing polymerase chain reaction conditions sufficient to amplify all or part of said nucleic acid molecule;

iv) analysing the amplified products of said polymerase chain reaction for the presence of a nucleic acid molecule comprising a nucleotide sequence derived from SEQ ID NO: 5 or 6; and optionally v) comparing the amplified product with a normal matched control.

According to a further aspect of the invention there is provided a prognostic method to monitor the severity of acute inflammation of the lung in response to a microbial infection in a subject comprising the steps:

i) providing an isolated biological sample to be tested;

ii) forming preparation comprising said cDNA and an oligonucleotide primer pair adapted to anneal to a nucleic acid molecule comprising a nucleotide sequence as set forth in SEQ ID NO: 5 or 6; a thermostable DNA polymerase, deoxynucleotide triphosphates and co-factors;

iii) providing polymerase chain reaction conditions sufficient to amplify all or part of said nucleic acid molecule;
iv) comparing the amplified product with a normal matched control; and
v) correlating the level of expression of expression of angiopoietin-related protein 4 as a measure of the severity of acute inflammation; and optionally
vi) designing or altering a treatment regimen for said subject.

In a preferred method of the invention said oligonucleotide primer pair comprises or consists essentially of the nucleotide sequences:

```
                                              [SEQ ID NO: 7]
forward (5'to 3'): TGGTTTGGCACCTGCAGCCATTC
and
                                              [SEQ ID NO: 8]
reverse (5'to 3'): TGCTGCCATGGGCTGGATCAAC.
```

In an alternative preferred method of the invention said oligonucleotide primer pair comprises or consists essentially of the nucleotide sequences:

```
                                              [SEQ ID NO: 9]
forward (5'to 3'): TCCAACGCCACCCACTTAC
and
                                              [SEQ ID NO: 10]
reverse (5'to 3'): TGAAGTCATCTCACAGTTGACCA.
```

In a preferred method of the invention said method is a real time PCR method for the detection and quantification of a nucleic acid encoding all or part of the nucleotide sequence set forth in SEQ ID NO: 5 or 6.

According to an alternative aspect of the invention there is provided a diagnostic method for determining if a subject has or is predisposed to acute inflammation of the lung in response to a microbial infection comprising:
  i) providing an isolated biological sample to be tested;
  ii) forming a preparation comprising said sample and an antibody, or antibodies, that specifically bind a polypeptide in said sample as represented by the amino acid sequences presented in SEQ ID NO: 1 2, 3 or 4 to form an antibody/polypeptide complex;
  iii) detecting the complex; and
  iv) comparing the expression of said polypeptide with a normal matched control.

According to a further aspect of the invention there is provided a prognostic method to monitor the severity of acute inflammation of the lung in response to a microbial infection in a subject comprising the steps:
  i) providing an isolated biological sample to be tested;
  ii) forming a preparation comprising said sample and an antibody, or antibodies, that specifically bind a polypeptide in said sample as represented by the amino acid sequences presented in SEQ ID NO: 1, 2, 3 or 4 to form an antibody/polypeptide complex;
  iii) detecting the complex;
  iv) comparing the expression of said polypeptide with a normal matched control.
  v) correlating the level of expression of angiopoietin-related protein 4 polypeptide as a measure of the severity of acute inflammation; and optionally
  vi) designing or altering a treatment regimen for said subject.

In a preferred method of the invention said biological sample is selected from the group consisting of: blood, blood plasma or serum, lymph fluid, saliva, sputum, lavage, bronchoaveolar lavage.

In a preferred method of the invention said method further comprises designing a treatment regimen for the prevention or treatment of a microbial infection as determined by the result of said diagnostic test.

In a preferred method of the invention said treatment regimen comprises administration of a ligand or pharmaceutical composition according to the invention.

In a preferred method of the invention said ligand is an antibody according to the invention.

In an alternative preferred method of the invention said detection method is repeated at or near the end of the treatment regimen to determine the effect of said treatment on the subject.

In a preferred method of the invention the treatment regimen is either continued or discontinued after determining the effect of the treatment regimen.

In a further preferred method of the invention an alternative different treatment regimen is designed after determining the effect of the treatment regimen.

According to a further aspect of the invention there is provided a method for preparing a hybridoma cell-line producing monoclonal antibodies according to the invention comprising the steps of:
  i) immunising an immunocompetent mammal with an immunogen comprising at least one polypeptide having the amino acid sequence as represented in SEQ ID NO: 1, 2, 3 or 4 or fragments thereof;
  ii) fusing lymphocytes of the immunised immunocompetent mammal with myeloma cells to form hybridoma cells;
  iii) screening monoclonal antibodies produced by the hybridoma cells of step (ii) for binding activity to the amino acid sequences of (i);
  iv) culturing the hybridoma cells to proliferate and/or to secrete said monoclonal antibody; and optionally
  v) recovering the monoclonal antibody from the culture supernatant.

Preferably, the said immunocompetent mammal is a mouse. Alternatively, said immunocompetent mammal is a rat.

According to a further aspect of the invention there is provided a method to screen a combinatorial antibody phage display library wherein said library comprises antibody variable heavy and variable light chain nucleic acids comprising the steps:
  i) contacting a phage display library expressing said antibody variable heavy and light chains with a polypeptide antigen comprising an amino acid sequence as set forth in SEQ ID NO: 1, 2, 3 or 4;
  ii) selecting phage that specifically bind the antigen;
  iii) repeating i) and ii) above to identify phage clones that bind said antigen until high affinity binders are selected; and optionally
  iv) isolating and storing said phage.

According to an aspect of the invention there is provided a hybridoma obtained or obtainable by the method according to the invention.

According to a further aspect of the invention there is provided a monoclonal antibody phage obtained or obtainable by the method according to the invention.

According to a further aspect of the invention there is provided a modelling method to determine the association of a ligand with angiopoietin-related protein 4 comprising the steps of:
  i) providing computational means to perform a fitting operation between an agent and a polypeptide comprising or consisting of an amino acid sequence as set forth in SEQ ID NO: 1, 2, 3 or 4; and ii) analysing the results of said fitting operation to quantify the association between the agent and the polypeptide.

The rational design of binding entities for proteins is known in the art and there are a large number of computer programs that can be utilised in the modelling of 3-dimensional protein structures to determine the binding of chemical entities to functional regions of proteins and also to determine the effects of mutation on protein structure. This may be applied to binding entities and also to the binding sites for such entities. The computational design of proteins and/or protein ligands demands various computational analyses which are necessary to determine whether a molecule is sufficiently similar to the target protein or polypeptide. Such analyses may be carried out in current software applications, such as the Molecular Similarity application of QUANTA (Molecular Simulations Inc., Waltham, Mass.) version 3.3, and as described in the accompanying User's Guide, Volume 3 pages. 134-135. The Molecular Similarity application permits comparisons between different structures, different conformations of the same structure, and different parts of the same structure. Each structure is identified by a name. One structure is identified as the target (i.e., the fixed structure); all remaining structures are working structures (i.e. moving structures). When a rigid fitting method is used, the working structure is translated and rotated to obtain an optimum fit with the target structure.

The person skilled in the art may use one of several methods to screen chemical entities or fragments for their ability to associate with a target. The screening process may begin by visual inspection of the target on the computer screen, generated from a machine-readable storage medium. Selected fragments or chemical entities may then be positioned in a variety of orientations, or docked, within the binding pocket.

Useful programs to aid the person skilled in the art in connecting the individual chemical entities or fragments include: CAVEAT (P. A. Bartlett et al, "CAVEAT: A Program to Facilitate the Structure-Derived Design of Biologically Active Molecules". In Molecular Recognition in Chemical and Biological Problems", Special Pub., Royal Chem. Soc., 78, pp. 182-196 (1989)). CAVEAT is available from the University of California, Berkeley, Calif. 3D Database systems such as MACCS-3D (MDL Information Systems, San Leandro, Calif.). This is reviewed in Y. C. Martin, "3D Database Searching in Drug Design", J. Med. Chem., 35, pp. 2145-2154 (1992); and HOOK (available from Molecular Simulations, Burlington, Mass.).

Once the agent has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. The computational analysis and design of molecules, as well as software and computer systems are described in U.S. Pat. No. 5,978,740 which is included herein by reference.

According to a further aspect of the invention there is provided a screening method for the identification of a ligand which inhibits the activity of angiopoletin-related protein 4 comprising the steps of:
  i) providing a polypeptide consisting of amino acid residues set forth in SEQ ID NO: 1,2, 3 or 4;
  ii) providing at least one candidate agent to be tested;
  iii) forming a preparation that is a combination of (i) and (ii) above; and
  iv) testing the effect of the ligand on the activity of angiopoietin-related protein 4.

According to a further aspect of the invention there is provided an in vivo screening method for the identification of a ligand which inhibits the expression or activity of angiopoietin-related protein 4 comprising the steps of:
  i) providing non-human mammal wherein the mammal has been infected with one or more microbial pathogens;
  ii) administering to the mammal one or more agents inhibiting the expression or activity of angiopoietin-related protein 4; and
  iii) monitoring the effect of the agent on the progression of the microbial infection In a preferred method of the invention said non-human mammal is a rodent; preferably a mouse, rat or hamster.

In a preferred method of the invention the expression or activity of angiopoietin-related protein 4 is monitored using the diagnostic method according to the invention.

According to a further aspect of the invention there is provided a binding agent according to the invention for use in the reduction of bleeding and/or oedema in a subject suffering from an inflammatory lung disease.

According to a further aspect of the invention there is provided a binding agent according to the invention for use in promoting and/or maintaining lung tissue integrity in a subject suffering from an inflammatory lung disease.

According to a further aspect of the invention there is provided a binding agent according to the invention for use promoting lung tissue differentiation and/or regeneration in a subject suffering from an inflammatory lung disease.

According to an aspect of the invention there is provided a method to treat an inflammatory lung disease comprising administering an effective amount of a binding agent according to the invention to a subject to reduce bleeding and/or oedema.

According to a further aspect of the invention there is provided a method to treat an inflammatory lung disease comprising administering an effective amount of a binding agent according to the invention to a subject to promote and/or maintain lung tissue integrity.

According to a further aspect of the invention there is provided a method to treat an inflammatory lung disease comprising administering an effective amount of a binding agent according to the invention to a subject to promote lung tissue differentiation and/or regeneration.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

An embodiment of the invention will now be described by example only and with reference to the following figures;

(FIG. 1C) Elevated expression of cAngptl4 was detected in damaged lung tissue, associated with the infiltration of immune cells. Representative whole lung images from 5 mice at each time point. Day 0 samples served as control. (FIG. 1D) Viral replication and spread were detected by immunohistochemistry on lung tissue sections. Viral replication peaks around day 5 post infection, and is eliminated by immune responses around day 9. (FIG. 1E) In alveolar spaces, viral replication mainly takes place in type II alveolar epithelial cells. (FIG. 1F) In responses to viral infection, macrophages and neutrophils infiltrate into alveolar spaces in significant amount at day 7. Lymphocytes were observed in abundance from day 9. These immune cell infiltration further increases tissue damage and causes oedema that peaks at day 13. (FIG. 1G) cANGPTL4 kinetics were summarized for mouse influenza infection. cANGPTL4 protein amount coincides in time scale with oedema. The well-characterized cANGPTL4 kinetics in influenza infection on mice help in the design of cANGPTL4 targeted treatment, and the design of study on the effect of cANGPTL4 in respiratory tract infection;

FIG. 2A refers to alveolar Space, FIG. 2B to blood vessel and FIG. 2C to bronchiole. H&E staining was used to show the tissue structure, and cAngptl4 was stained using anti-cAngptl4 antibody (green). In control mice, no inflamed region and little cAngptl4 expression can be detected in alveolar spaces. The expression of cAngptl4 was restricted to the well-defined blood vessel structure. For infected mice, dense staining in H&E marked lung regions that were heavily infiltrated by immune cells at day 5 and 13 post infection, which is a typical event in inflammation and caused local lung damage. In contrast to control mice, the expression of cAngptl4 is not limited to endothelium, but was extensively detected in the lung regions of massive infiltration of immune cells. Bronchioles consistently express cANGPTL4 throughout the entire disease progression;

Microarray data showed reduction of inflammatory responses, cytokine stimulus, hormone stimulus and peptide hormone stimulus by the antibody treatment, which reflects the effect following the neutralization of cANGPTL4 with antibody injection. Moreover, inhibition on extracellular matrix related activities was also observed, indicating a reduced risk for lung fibrosis with antibody treatment.

Figure 9A:
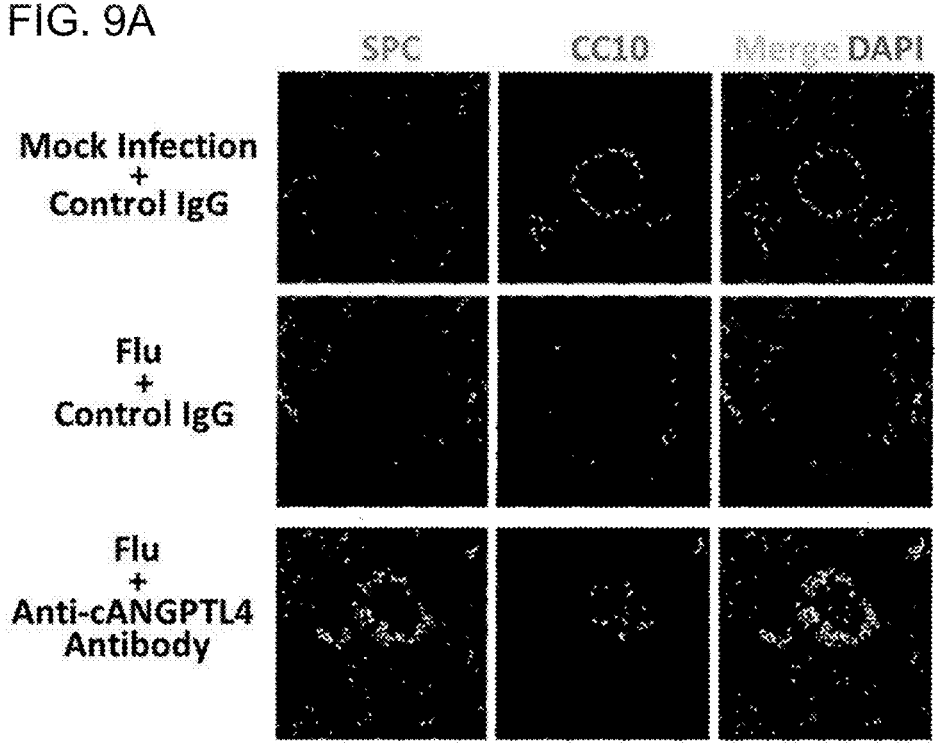
Figure 9B:
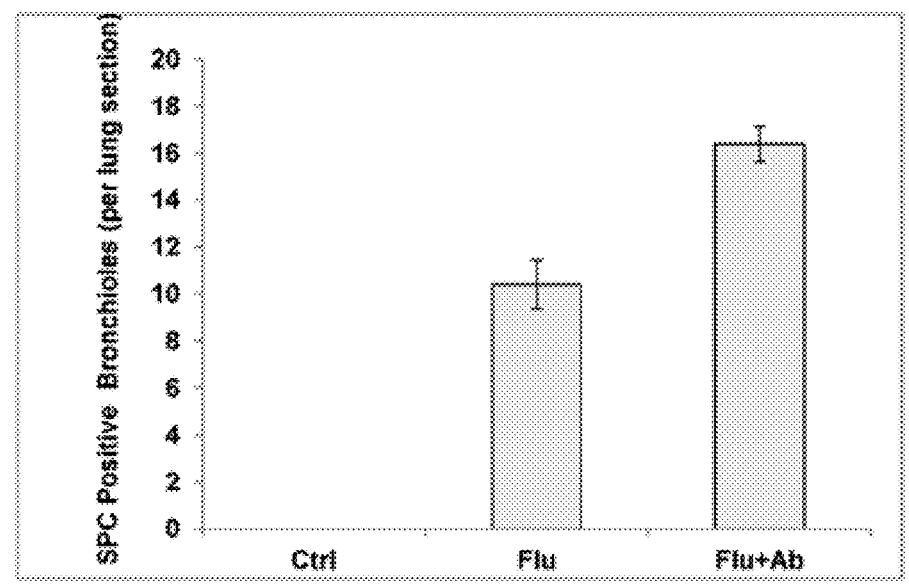
Figure 9C:
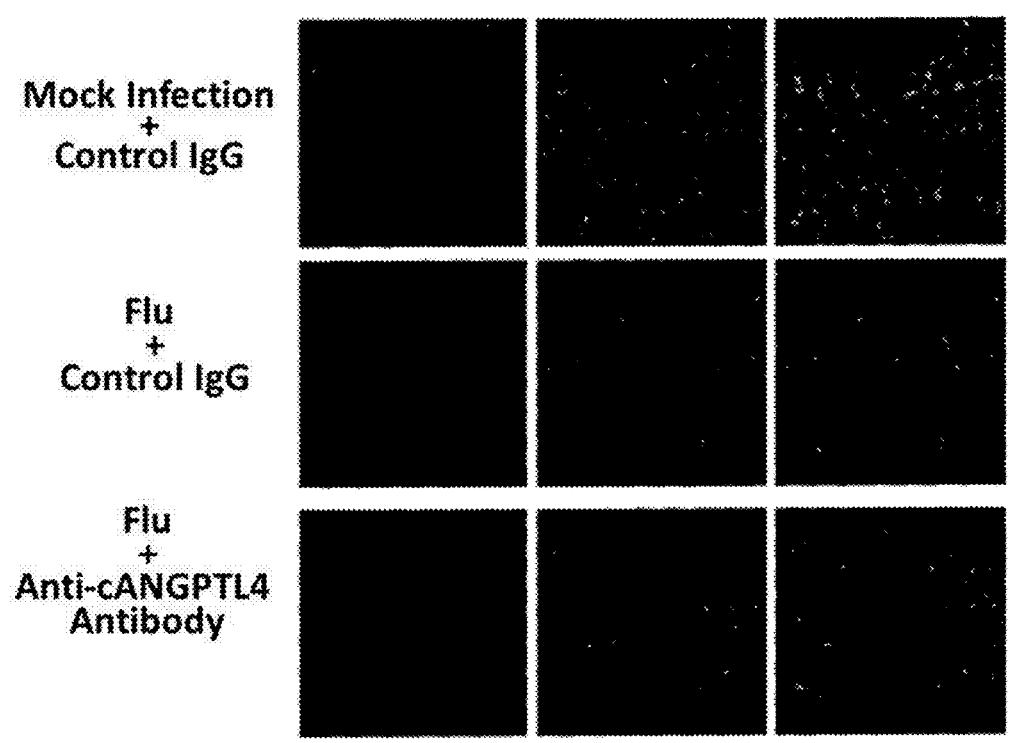

FIGS. 9A-9C: Tissue differentiation and regeneration were enhanced in anti-cANGPTL4 antibody treated mouse lung samples following influenza infection (FIG. 9A) Staining with CC10 (Clara cell marker) and SPC (Type II alveolar epithelial cell marker) shows that in anti-cANGPTL4 antibody treated influenza infected mouse lung samples there is increased Clara cells differentiation into SPC positive cells compared with control IgG treated influenza infected mouse lung samples, which was shown as an important process that repairs damaged alveolar spaces [Zheng D, et al 2012]. (FIG. 9B) A significant increase effect in this differentiation process in anti-cANGPTL4 antibody treated influenza infected mouse sample was shown compared with control IgG treated influenza infected mouse sample by calculating the amount of differentiated bronchioles in each lung section from all the five mouse samples in each experimental group. (FIG. 9C) Lung sections with anti-cANGPTL4 treatment and influenza infection also showed better PDPN regeneration in infiltrated lung regions than control IgG-treated influenza infected lung sections, indicating better tissue regeneration in anti-cANGPTL4 treated mice following influenza infection.

SEQUENCE LISTING

The Sequence Listing is submitted as an Annex C/St.25 text file, named "Sequence.txt," created on Jul. 16, 2015, ~16 kb, which is incorporated by reference herein.

Definitions

Pharmaceutical Compositions

The compositions of the present invention are administered in pharmaceutically acceptable preparations. Such preparations may routinely contain pharmaceutically acceptable concentrations of salt, buffering agents, preservatives, compatible carriers and supplementary anti-bacterial, anti-viral agents or anti-fungal agents.

The compositions of the invention can be administered by any conventional route, including injection or by gradual infusion over time. The administration may, for example, be oral, nasal, intravenous, intraperitoneal, intramuscular, intra-cavity, subcutaneous, transdermal, trans-epithelial.

The compositions of the invention are administered in effective amounts. An "effective amount" is that amount of a composition that alone, or together with further doses, produces the desired response. In the case of treating a particular disease, such as an inflammatory lung disease, the desired response is inhibiting the progression of the disease. This may involve only slowing the progression of the disease temporarily, although more preferably, it involves halting the progression of the disease permanently. This can be monitored by routine methods or by using the diagnostic assay according to the invention.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of an agent according to the invention for producing the desired response in a unit of weight or volume suitable for administration to a patient.

The doses of the ligand/antibody according to the invention administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. Other protocols for the administration of compositions will be known to one of ordinary skill in the art, in which the dose amount, schedule of injections, sites of injections, mode of administration and the like vary from the foregoing. The administration of compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep, goat, dog, cat or rodent.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents' (e.g. anti-inflammatory agents such as steroids, non-steroidal anti-inflammatory agents or antibiotics). When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Compositions may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" in this context denotes an organic or inorganic ingredient, natural or synthetic, with which the active ingredient is combined to facilitate the application, (e.g. liposome or immuno-liposome). The components of the pharmaceutical compositions also are capable of being co-mingled with the ligands of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride, chlorobutanol, parabens and thimerosal. The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as syrup, elixir or an emulsion or as a gel.

Compositions may be administered as aerosols and inhaled.

Compositions suitable for parenteral administration conveniently comprise a sterile aqueous or non-aqueous preparation of agent, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

Antibodies and Antibody Fragments

Antibodies include polyclonal and monoclonal antibodies, prepared according to conventional methodology. The production of monoclonal antibodies using hybridoma cells is well-known in the art. The methods used to produce monoclonal antibodies are disclosed by Kohler and Milstein in Nature 256, 495-497 (1975) and also by Donillard and Hoffman, "Basic Facts about Hybridomas" in Compendium of Immunology V.II ed. by Schwartz, 1981.

Chimeric antibodies are recombinant antibodies in which all of the V-regions of a mouse or rat antibody are combined with human antibody C-regions. Humanised antibodies are recombinant hybrid antibodies which fuse the complementarity determining regions from a rodent antibody V-region with the framework regions from the human antibody V-regions. The C-regions from the human antibody are also used. The complementarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanised antibodies have reduced antigenicity when injected to a human subject because there is a reduced amount of rodent (i.e. foreign) antibody within the recombinant hybrid antibody, while the human antibody regions do not elicit an immune response. This results in a weaker immune response and a decrease in the clearance of the antibody. This is clearly desirable when using therapeutic antibodies in the treatment of human diseases. Humanised antibodies are designed to have less "foreign" antibody regions and are therefore thought to be less immunogenic than chimeric antibodies.

Various fragments of antibodies are known in the art. A Fab fragment is a multimeric protein consisting of the immunologically active portions of an immunoglobulin heavy chain variable region and an immunoglobulin light chain variable region, covalently coupled together and capable of specifically binding to an antigen. Fab fragments are generated via proteolytic cleavage (with, for example, papain) of an intact immunoglobulin molecule. A $Fab_2$ fragment comprises two joined Fab fragments. When these two fragments are joined by the immunoglobulin hinge region, a $F(ab')_2$ fragment results. An Fv fragment is multimeric protein consisting of the immunologically active portions of an immunoglobulin heavy chain variable region and an immunoglobulin light chain variable region covalently coupled together and capable of specifically binding to an antigen. A fragment could also be a single chain polypeptide containing only one light chain variable region, or a fragment thereof that contains the three CDRs of the light chain variable region, without an associated heavy chain variable region, or a fragment thereof containing the three CDRs of the heavy chain variable region, without an associated light chain moiety; and multi specific antibodies formed from antibody fragments, this has for example been described in U.S. Pat. No. 6,248,516. Fv fragments or single region (domain) fragments are typically generated by expression in host cell lines of the relevant identified regions. These and other immunoglobulin or antibody fragments are within the scope of the invention and are described in standard immunology textbooks such as Paul, *Fundamental Immunology* or Janeway et al. *Immunobiology* (cited above). Molecular biology now allows direct synthesis (via expression in cells or chemically) of these fragments, as well as synthesis of combinations thereof. A fragment of an antibody or immunoglobulin can also have bispecific function as described above.

Materials and Methods

Mice and Infection.

Female C57BL/6J mice aged 8 to 12 weeks old were purchased from Biological resource centre, Biopolis. H1N1 influenza virus A/PR/8/34 strain (PR8) was purchased from American Type Culture Collection (ATCC). The virus was propagated in embryonated chicken egg. Virus titration was done by plaque assay using infection on Madin-Darby Canine Kidney (MDCK) cells. A sub-lethal dose of PR8 at 30 PFU was used for infection on each mouse. Virus was delivered into the trachea of the mice in 75 µl of phosphate buffered saline (pH 7.4). Mouse lung tissues were harvested from euthanized mice at selected time points and fixed for 24 hours in 10% neutral buffered formalin (from Sigma-Aldrich) for immunohistochemistry staining or frozen at −80° C. until RNA and protein extraction. The described animal work was approved by the Institutional Animal Care and Use Committee of National University of Singapore with IACUC Number 050/11.

For mouse study involving *S. Pneumoniae* infection, 8-12 weeks old, female Balb/c mice were used and the influenza virus used was mouse-adapted influenza A/Aichi/2/68 (H3N2) virus. The original stock of virus from the American Type Culture Collection (Manassas, Va., USA) was adapted in female BALB/c mice through serial lung-to-lung passaging. A sublethal dose of 1500 PFU of the virus was used for infection as described in previous section. All animal protocols were approved by the Institutional Animal Care and Use Committee, National University of Singapore (IACUC Number 050/11) and the Institutional Animal Care and Use Committee, Nanyang Technological University (IACUC number ARF SBS/NIE-A0200AZ).

Mice were either infected with heat-inactivated influenza virus and 1000 CFU heat-inactivated *S. Pneumoniae*, with 1000 CFU of *S. Pneumoniae* only, with influenza virus only, or with 1000 CFU *S. Pneumoniae* at 7 days post influenza infection. Samples were harvested for immunohistochemical staining at day 9 post infection starting from the initial infection with influenza or heat-infected influenza and heat-inactivated *S. Pneumoniae*.

Bronchial Lavage Fluid collection. Bronchial Lavage Fluid (BALF) was obtained from mice by injecting 0.5 mL 1x PBS into the trachea of the mice. The injected PBS was collected back by the syringe and transferred into eppendorf tubes. Each mouse was performed twice and the BALF obtained was combined and stored inside −80 degree freezer.

Antibody Treatment on Mice.

Anti-cANGPTL4 monoclonal antibody was produced in our lab using hybridoma as described in previous publication [Zhu et al, 2011]. Mice were intraperitonally injected with the antibody in 200 µL saline every day at a dose of 10 mg/kg body weight on day 6-10 post infection (harvested on day 11) or on day 13 to 17 post infection (harvested on day 18).

Antibody Information.

Anti-cANGPTL4 antibodies were produced in our lab as previously described [Zhu et al, 2011]. Other primary antibodies include influenza NS1 (Santa Cruz, sc130568), Pdpn (R&D Systems, AF3244), SPC (Santa Cruz, sc13979) and CC10 (Santa Cruz, sc9772).

In Vivo Imaging of Mice.

Mice were either mock infected with heat-inactivated influenza virus, infected with influenza virus and injected with control IgG, or infected with influenza virus and treated with anti-cANGPTL4 antibody on day 13 to 17 post infection as described in previous section. At the day of harvesting, mice were injected through tail vein with IRDye® 800CW PEG Contrast Agent (Licor 926-50401) following manufacturer's instructions and imaged by in vivo imaging under anesthesia, using Licor MousePOD® in vivo Imaging facility. Following the in vivo imaging, the lungs of the mice were harvested and imaged again.

Quantitative Real-Time RT-PCR.

Frozen tissues were extracted for total RNA using Qiagen RNeasy mini kit together with Qiagen DNaseI enzyme treatment. RNA concentration was measured using ND-1000 spectrophotometer from NanoDrop Technologies. Reverse-transcription was performed using oligo(dT) and iScript reverse transcriptase from Bio-rad. According to the manufacturer's instructions, PCR was performed using Bio-rad Ssofast Evagreen Supermix on Bio-rad CFX-96 real-time system. Primers used for ANGPTL4 detection are:

Forward (5' to 3'): TCCAACGCCACCCACTTAC (SEQ ID No 9); Reverse (5' to 3'): TGAAGTCATCTCACAGTT-GACCA (SEQ ID No 10).

Immunoblotting.

For protein extraction, harvested and frozen-preserved mouse lung tissues were treated with 2× Laemmli sample buffer without bromophenol blue. Obtained protein concentration was determined and normalized by adjusting β-tubulin. Protein samples were separated by SDS-PAGE and transferred to nitrocellulose membranes (Bio-rad).

Immuno Histochemistry Staining.

Formalin-fixed lung tissues were processed and embedded in paraffin using Leica tissue processor and embedding station. Lung tissue sections were cut at 5 µm thickness and mounted onto poly-L-lysine coated slides from Thermal Fisher Scientific. Slides were de-waxed and rehydrated before staining. Antigen retrieval was done by digestion for 25 minutes at 37° C. in proteinase K solution from Sigma Aldrich (20 µg/ml proteinase K in 50 mM Tris-HCl, with 1 mM EDTA, pH 8.0). Primary antibody incubation was done overnight at 4° C., and fluorescence secondary antibody incubation was done for 1 h at room temperature. Anti-fade reagent with DAPI from Invitrogen was used for slide mounting. The slides were either scanned by Carl Zeiss MIRAX MIDI system or taken picture by fluorescence microscope Carl Zeiss Observer Z1 for immunohistology details.

Microarray Analysis.

Mice were infected with influenza virus and treated with either control IgG or anti-cANGPTL4 antibody on day 13 to 17 post infection as described in previous section. Lungs were harvested at Day 12 (for mice with only infection), Day 14 (for mice with infection and treated with either control IgG or anti-cANGPTL4 antibody), and Day 18 post infection (for mice with infection and treated with either control IgG or anti-cANGPTL4 antibody). RNA was extracted from the lungs with Trizol following manufacturer's protocol. Further sample processing of the RNA was done using Applause® WT-Amp ST System from NuGEN, and microarray experiment was done on GeneChip® Mouse Gene 1.0 ST Arrays according to manufactuer's instructions.

Clinical Samples.

Paraffin blocks from patients with normal non-inflamed lungs and patients with pneumonia were obtained from the Department of Pathology, National University Hospital (NUH). Approval from Institutional Review Board (IRB) has been obtained for this experiment design (2012/00661 Investigation of cANGPTL4 as a biomarker for inflammation-induced acute lung damage). All the slides were immunostained for cANGPTL4 under the same condition as described above.

Example 1 cAngptl4 Expression During Inflammation-Induced Lung Damage (FIG. 1)

Mice were infected with PR8 virus and lungs were harvested at indicated days post infection. Each time point includes samples from 5 mice. The (a) mRNA and (b) protein expression profile of cAngptl4 in mouse lung tissue during acute lung damage induced by inflammation, as determined by qPCR and immunodetection, respectively. The peak mRNA expression coincided with the commencement of acute lung damage induced by inflammation. The upregulation of ANGPTL4 mRNA expression also follows closely with the increase of viral replication. Highest cAngptl4 protein expression was observed at day 13 post infection, which coincided with extensive lung damage caused by inflammation in influenza infection. (c) Elevated expression of cAngptl4 was detected in damaged lung tissue, associated with the infiltration of immune cells. Representative whole lung images from 5 mice at each time point. Day 0 samples served as control. (d) Viral replication and spread were detected by immunohistochemistry on lung tissue sections. Viral replication peaks around day 5 post infection, and is eliminated by immune responses around day 9. (e) In alveolar spaces, viral replication mainly takes place in type II alveolar epithelial cells. (f) In responses to viral infection, macrophages and neutrophils infiltrate into alveolar spaces in significant amount at day 7. Lymphocytes were observed in abundance from day 9. These immune cell infiltration further increases tissue damage and causes oedema that peaks at day 13. (g) cANGPTL4 kinetics were summarized for mouse influenza infection. cANGPTL4 protein amount coincides in time scale with oedema. The well-characterized cANGPTL4 kinetics in influenza infection on mice help in the design of cANGPTL4 targeted treatment, and the design of study on the effect of cANGPTL4 in respiratory tract infection.

Figure 1A:
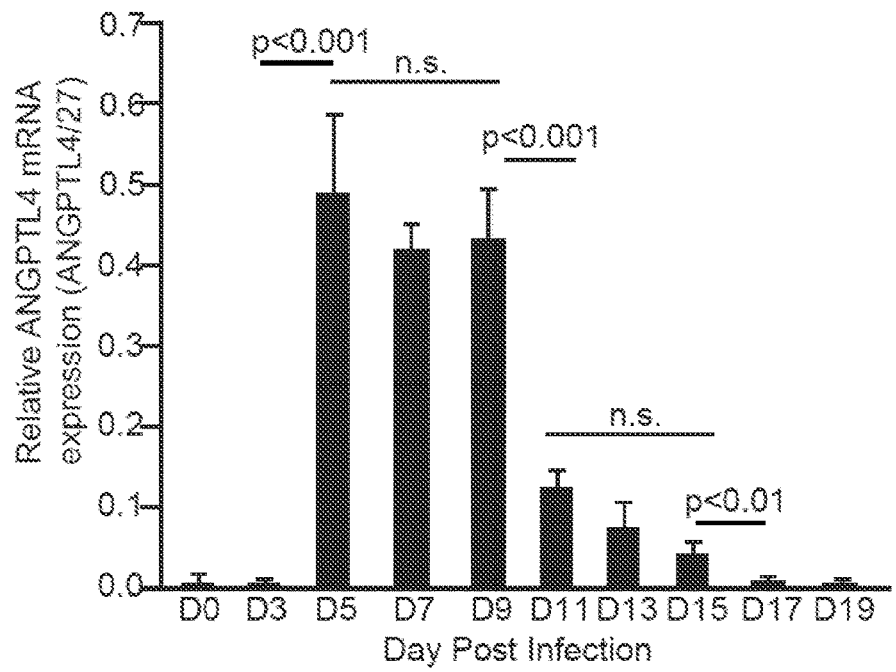
FIGS. 1A-1G: cAngptl4 Expression During Inflammation-induced Lung Damage. Mice were infected with PR8 virus and lungs were harvested at indicated days post infection. Each time point includes samples from 5 mice. The (FIG. 1A) mRNA and (FIG. 1B) protein expression profile of cAngptl4 in mouse lung tissue during acute lung damage induced by inflammation, as determined by qPCR and immunodetection, respectively. The peak mRNA expression coincided with the commencement of acute lung damage induced by inflammation. Highest cAngptl4 protein expression was observed at day 13 post infection, which coincided with extensive lung damage caused by inflammation in influenza infection.
Figure 1B:
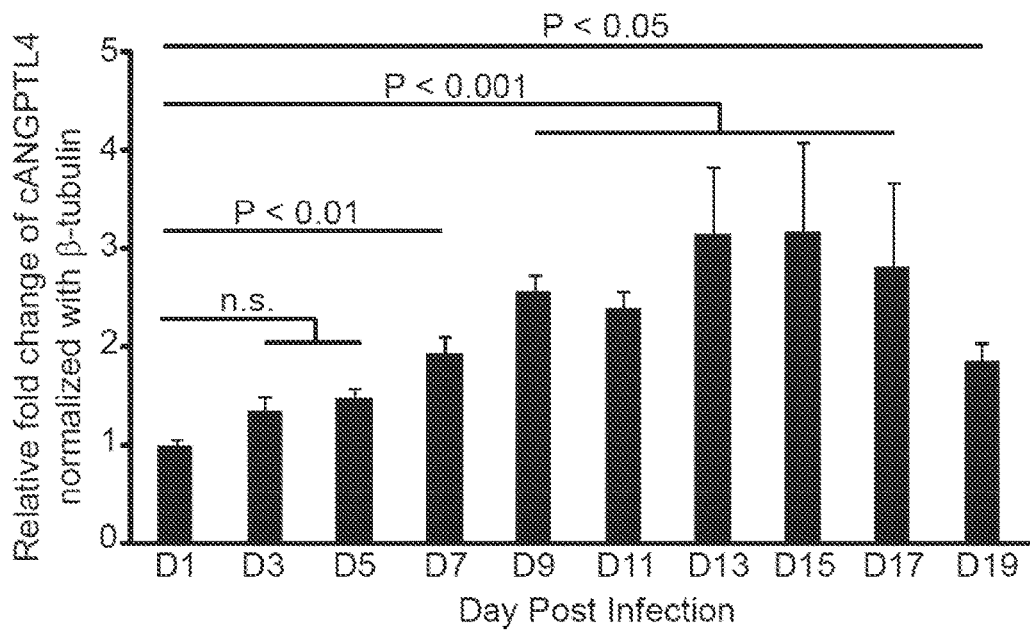
Figure 1C:
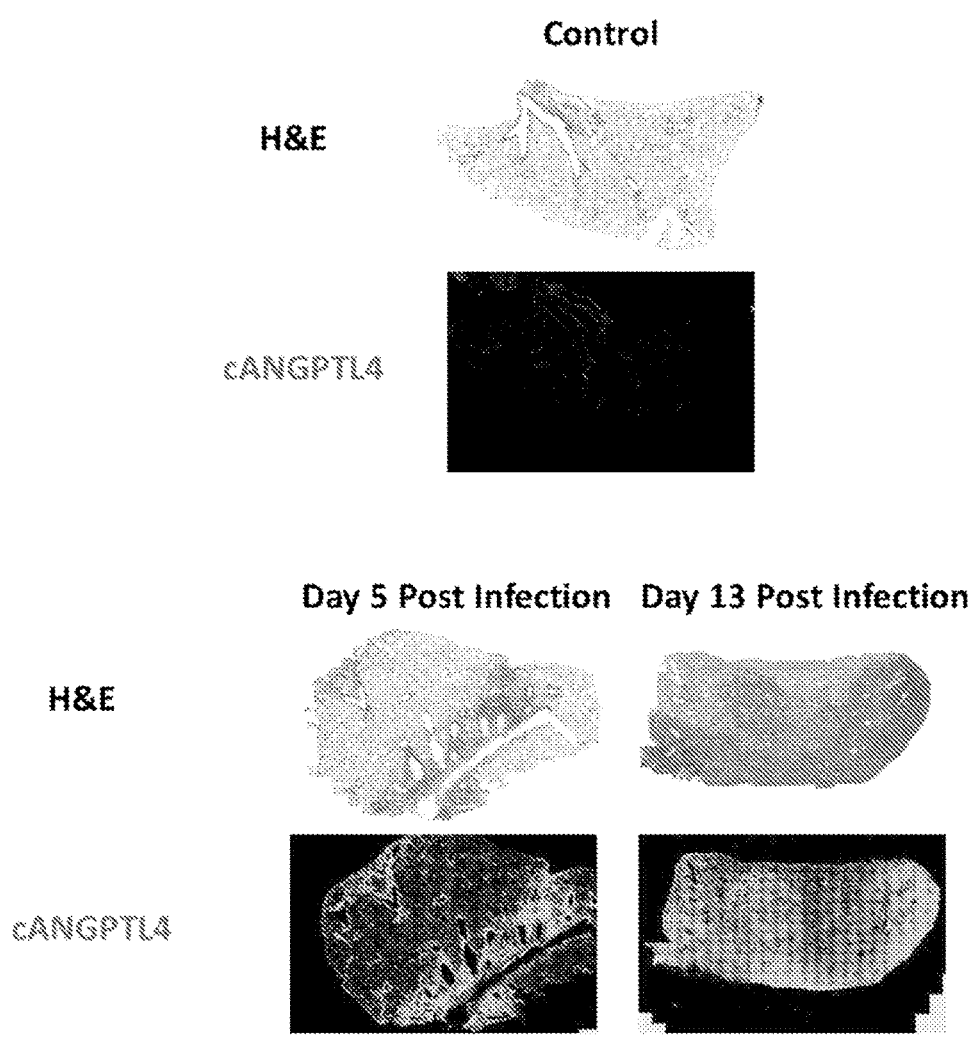
Figure 1D:
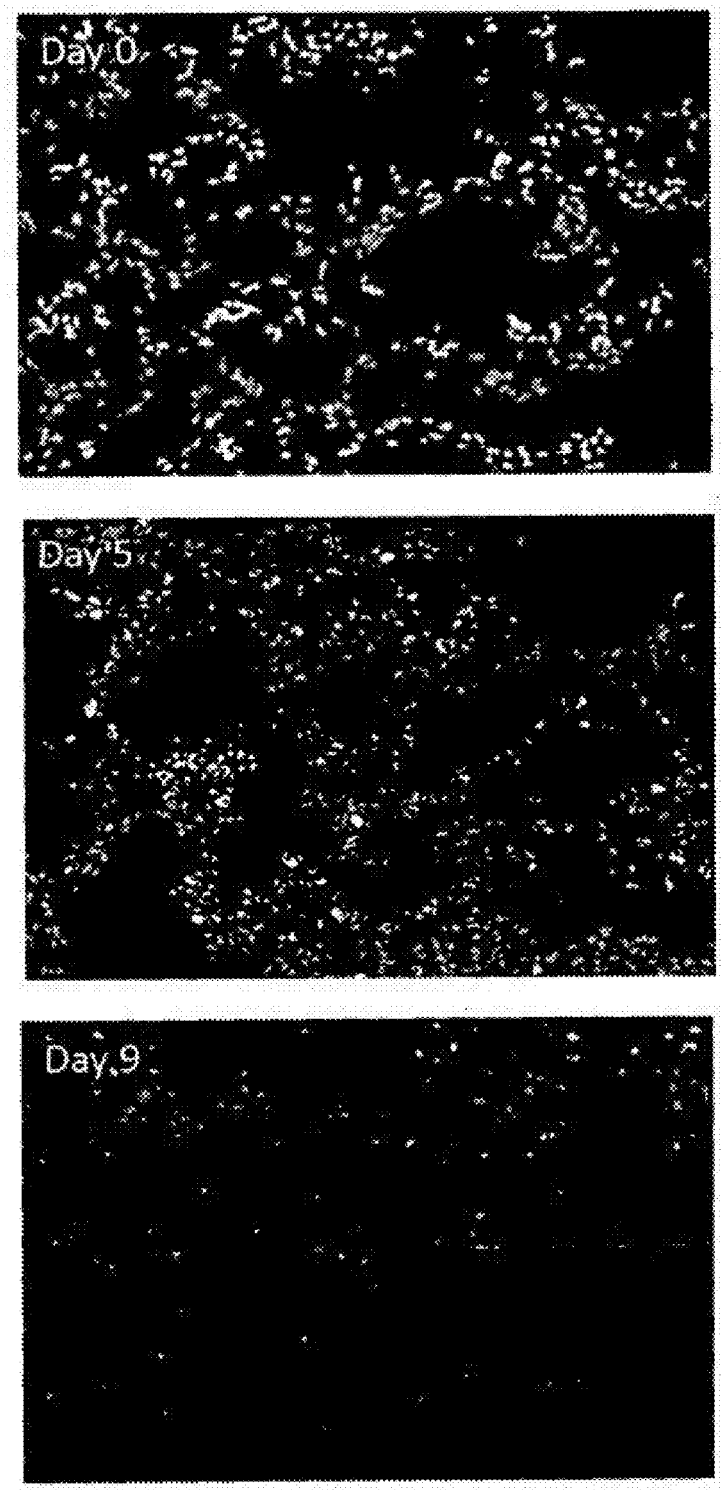
Figure 1E:
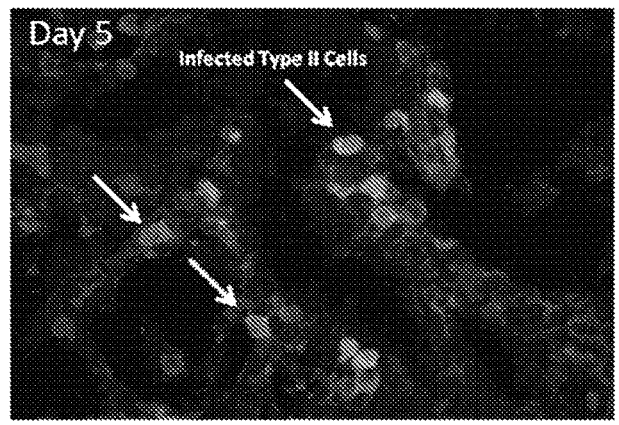
Figure 1F:
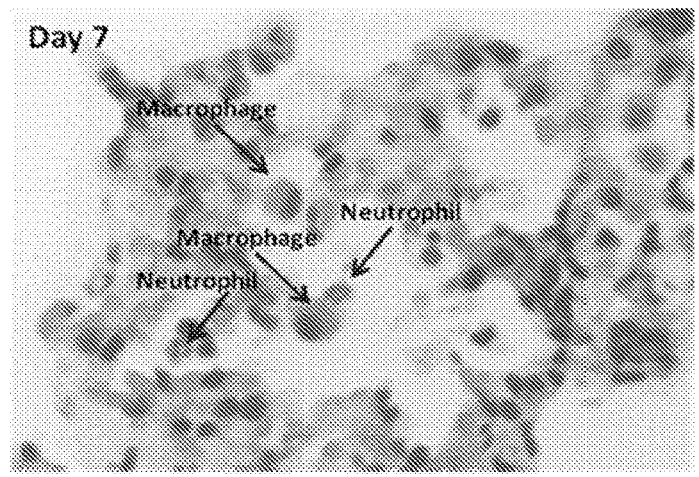
Figure 1F:
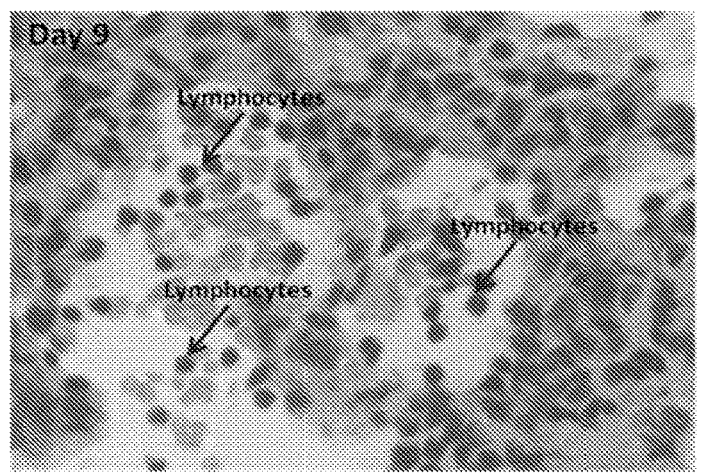
Figure 1G:
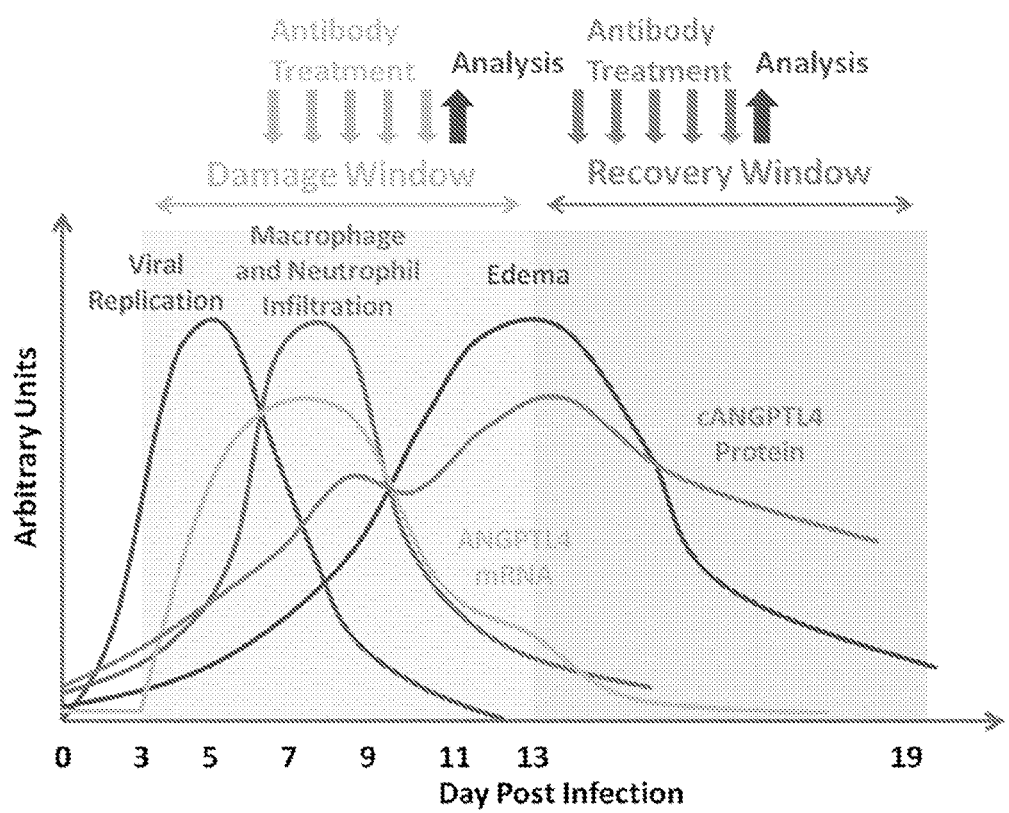
Figure 2A:
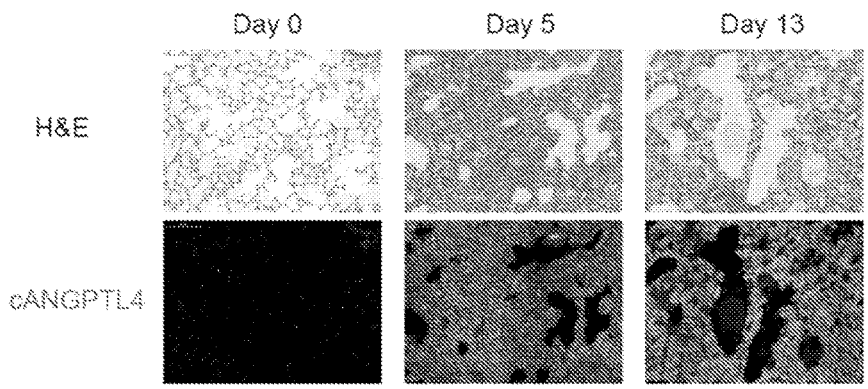
FIGS. 2A-2C: cAngptl4 Expression Coincides and Co localizes with Inflammation-induced Lung Damage in Influenza Infection on Mice. Mice were infected with PR8 virus and lungs were harvested at day 0 (used as control), day 5 and day 13 post infection. Each picture is the representative of 5 whole lung staining.
Figure 2B:
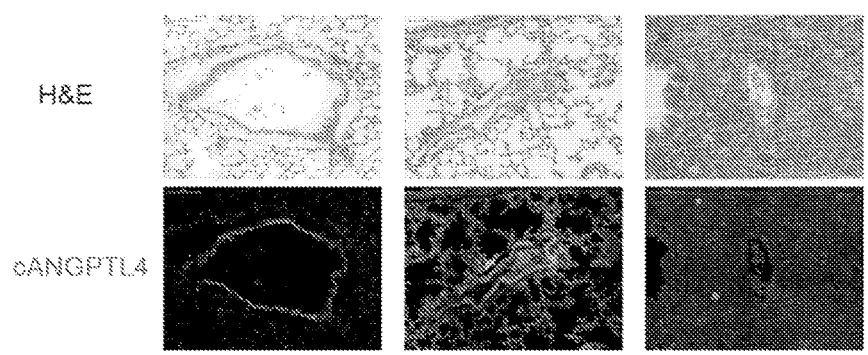
Figure 2C:
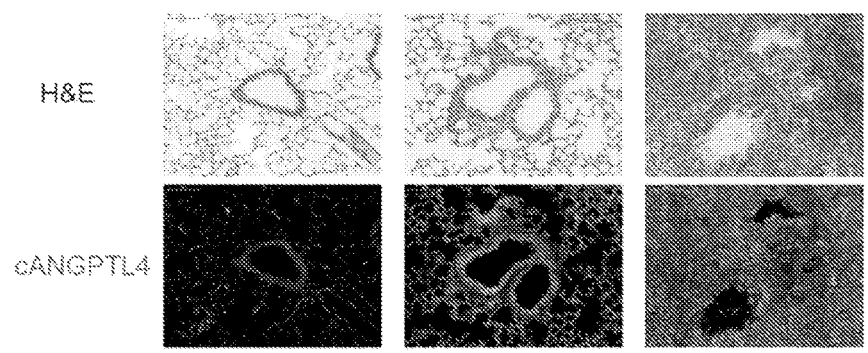

Example 2 cAngptl4 Expression Coincides and Co Localizes with Inflammation-Induced Lung Damage in Influenza Infection on Mice (FIG. 2)

Mice were infected with PR8 virus and lungs were harvested at day 0 (used as control), day 5 and day 13 post infection. In control mice, no inflamed region and little cAngptl4 expression can be detected in alveolar spaces. The expression of cAngptl4 was restricted to the well-defined blood vessel structure. For infected mice, dense staining in H&E marked lung regions that were heavily infiltrated by immune cells at day 5 and 13 post infection, which is a typical event in inflammation and caused local lung damage. In contrast to control mice, the expression of cAngptl4 is not limited to blood vessels, but was extensively detected in the lung regions of massive infiltration of immune cells. Bronchioles consistently express cANGPTL4 throughout the entire disease progression.

Example 3

Figure 3B:
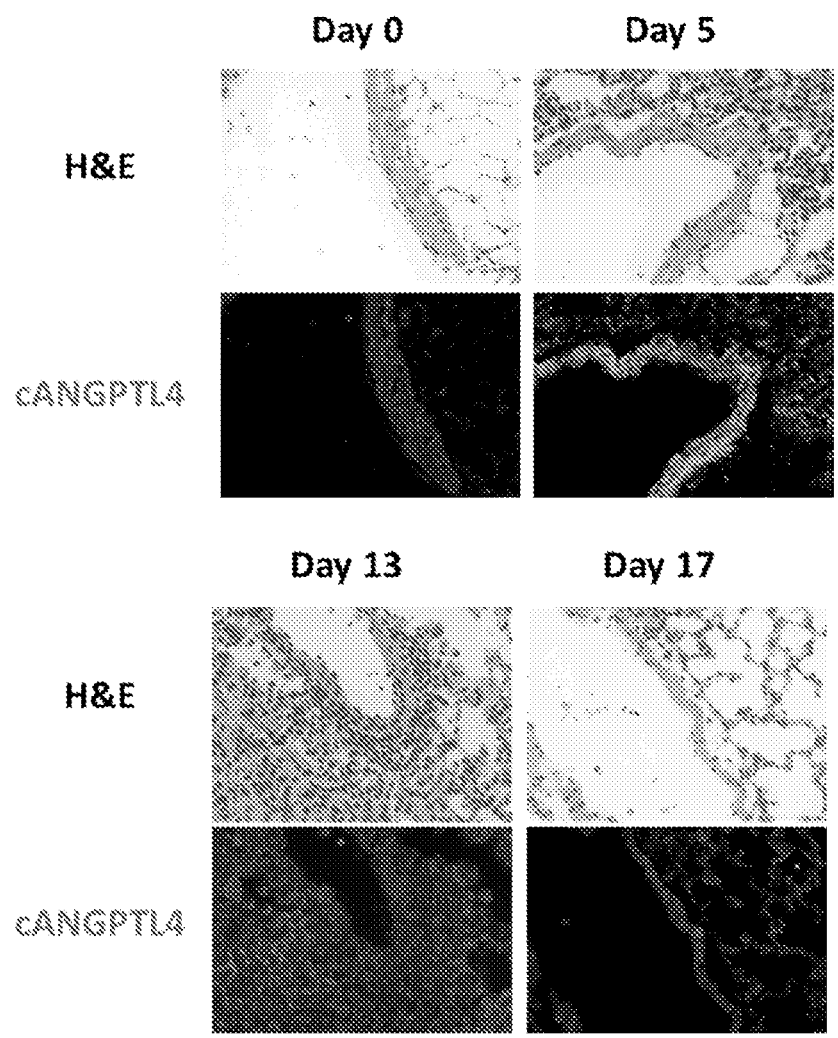
FIG. 3: Identification of the Source for cANGPTL4 Production during Influenza Infection (a) Consistent staining of cANGPTL4 on Clara cells; (b) Significantly increased anti-cANGPTL4 staining on tunical media at day 5 post infection; (c) Infected type II alveolar epithelial cells produce cANGPTL4.
Figure 4A:
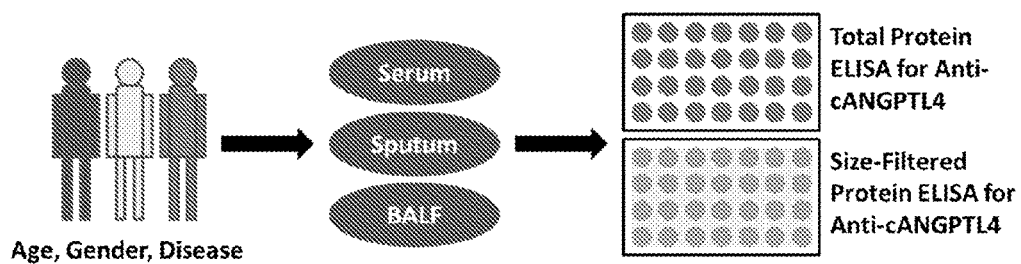
FIG. 4: cANGPTL4 Detection in Various Forms of Samples. (a) cANGPTL4 is a secreted protein and is expected to be detected from samples in various forms of body fluids and airway secretions including but not limited to serum, sputum and Bronchial Lavage Fluid [BALF], allowing convenient diagnosis using protein detection methods such as western blot or ELISA for cANGPTL4; (b) cANGPTL4 was detected in BALF protein by western blot using anti-cANGPTL4 antibody. The BALF was collected from PR8 influenza-infected mice at different time point post infection. Day 11 and Day 13 samples have significantly more cANGPTL4 than Day 0 protein, showing cANGPTL4 can be conveniently detected from airway secretions.
(FIG. 4C) Secondary infection following flu infection increases cANGPTL4 expression in mouse model. For mice mock infected with heat-inactivate influenza virus and S. Pneumoniae, cANGPTL4 signal was only detected at bronchioles but not in other regions such as alveolar space. For mice infected with 1000 CFU S. Pneumoniae only, similar cANGPTL4 signal was observed as those with mock infection. For mice infected with influenza only, at day 9 post infection a large portion of the lung was infiltrated and showed high level of cANGPTL4 protein. For mice with secondary S. Pneumoniae infection following influenza infection, the alveolar spaces were more infiltrated than the influenza infected mice, resulting in more cANGPTL4 protein stained.
(FIG. 4D) In clinical human lung biopsies, acute infection and inflammation give the most cANGPTL4 protein expression and can distinguish from chronic infection and inflammation.
Figure 4B:
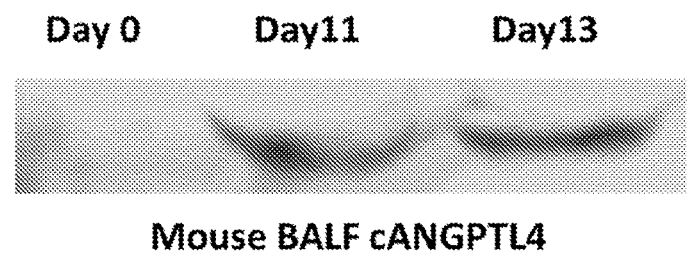
Figure 4C:
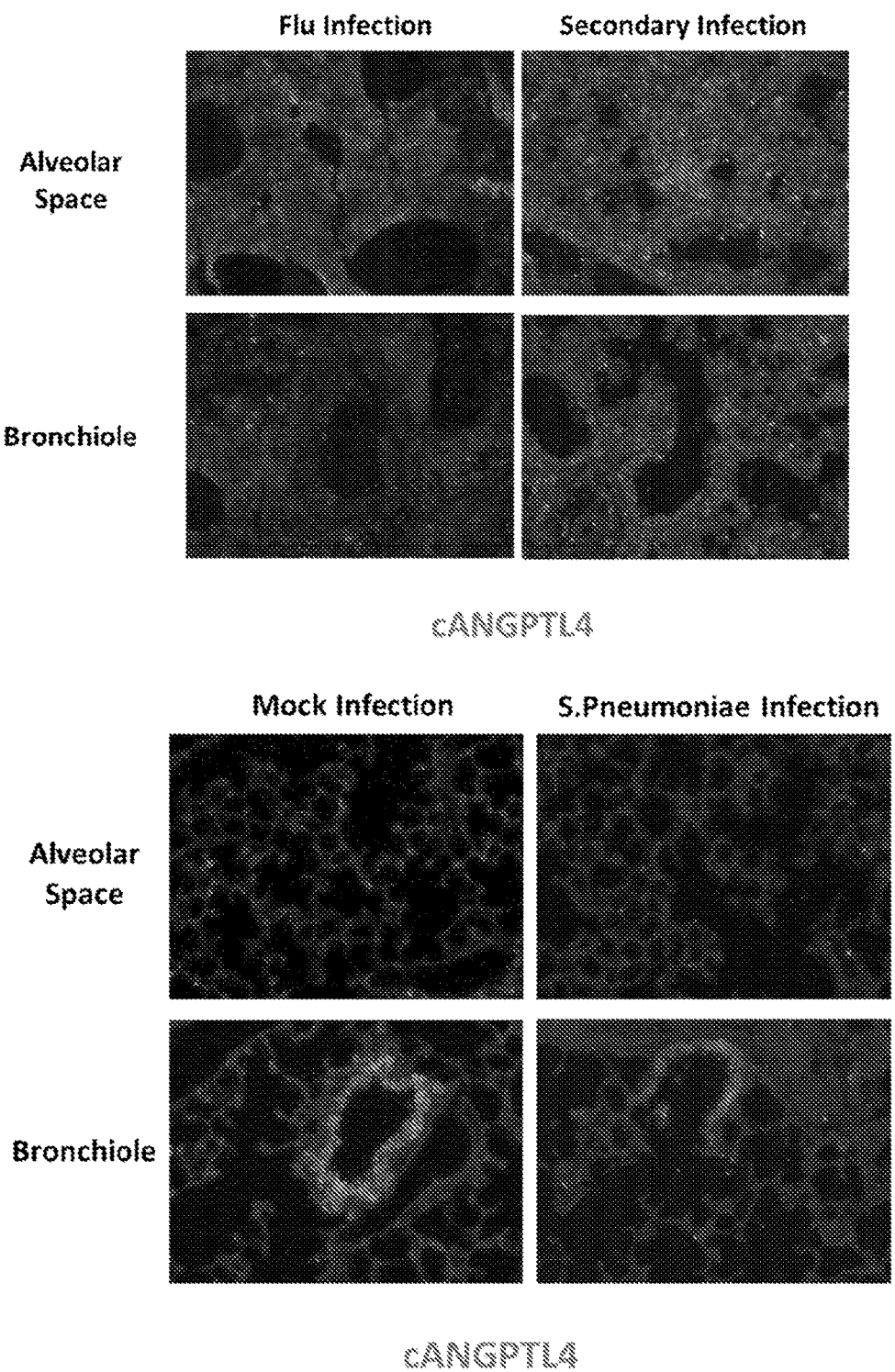
Figure 4D:
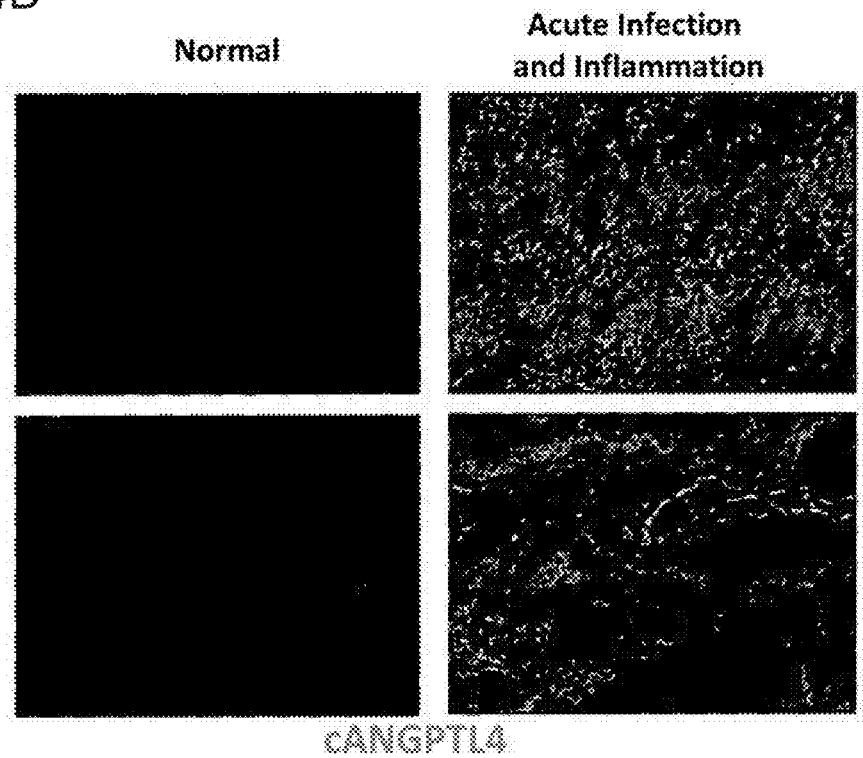
Figure 4D:
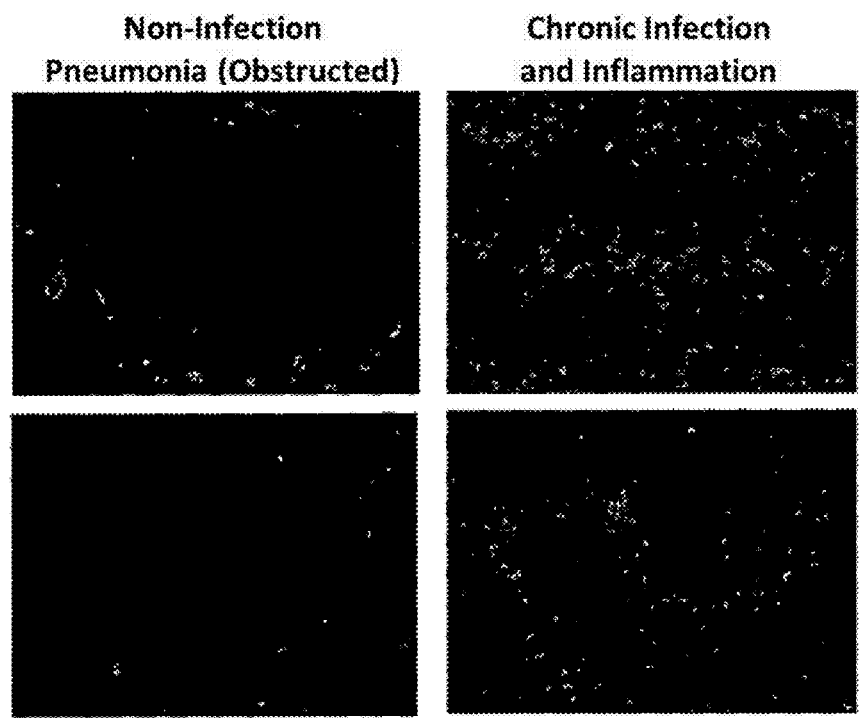

Identification of the Source for cANGPTL4 Production During Influenza Infection (FIG. 3)

The lung tissue sections were further analyzed to identify the main sources for cANGPTL4. (a) Dual immunohistochemistry staining was performed using major cell markers and cANGPTL4. Clara cells (CC10 positive) were shown to be consistently stained with anti-cANGPTL4 antibody throughout the disease progression. (b) Tunica media of the blood vessels was also shown to be stained with anti-cANGPTL4 antibody for the entire disease progression, while day 13 inflammation makes the staining of cANGPTL4 on tunica media less distinguishable from the surrounding tissues that are also stained with cANGPTL4. Tunica media at day 5 showed much higher staining of cANGPTL4 than the other time points, indicating active production of ANGPTL4. (c) Infected type II alveolar epithelial cells produces cANGPTL4 while non-infected type II alveolar epithelial cells do not.

Example 4 cANGPTL4 Detection in Various Forms of Samples. (FIG. 4)

(a) cANGPTL4 is a secreted protein and is expected to be detected from samples in various forms including serum, sputum and BALF, allowing convenient diagnosis using methods such as western blot or size-filtered protein ELISA for cANGPTL4; (b) cANGPTL4 was detected in BALF protein by western blot using anti-cANGPTL4 antibody. The BALF was collected from PR8 influenza-infected mice at different time point post infection. Day 11 and Day 13 samples have significantly more cANGPTL4 than Day 0 protein, showing cANGPTL4 can be conveniently detected from airway secretions. (c) Secondary infection following flu infection increases cANGPTL4 expression in mouse model. For mice mock infected with heat-inactivate influenza virus and *S. Pneumoniae*, cANGPTL4 signal was only detected at bronchioles but not in other regions such as alveolar space. For mice infected with 1000 CFU *S. Pneumoniae* only, similar cANGPTL4 signal was observed as those with mock infection. For mice infected with influenza only, at day 9 post infection a large portion of the lung was infiltrated and showed high level of cANGPTL4 protein. For mice with secondary *S. Pneumoniae* infection following influenza infection, the alveolar spaces were more infiltreated than the influenza infected mice, resulting in more cANGPTL4 protein stained; (d) In clinical human lung biopsies, patient samples with acute infection and inflammation were observed for the most cANGPTL4 protein expression. Patient samples with chronic infection and inflammation were observed for much less cANGPTL4 protein expression. Patient samples with non-infection pneumonia give least cANGPTL4 protein staining, similar as that of lung samples with no pneumonia.

Example 5

Figure 5:
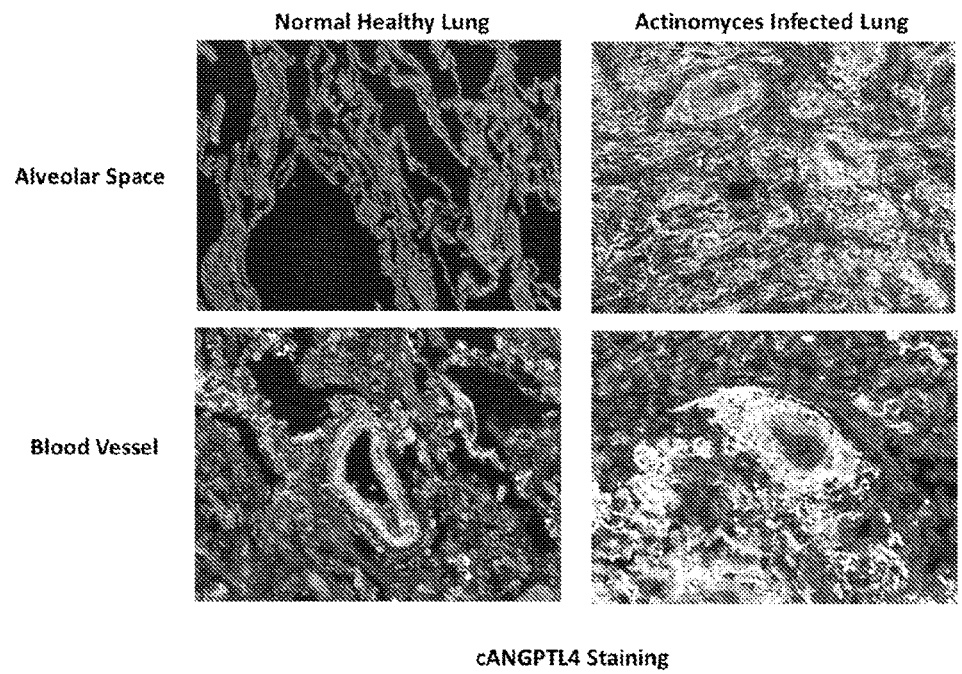
FIG. 5: Clinical Sample Analysis (with Bacterial Pneumonia) Reveals Similar cANGPTL4 Upregulation Pattern as in Influenza Pneumonia. *Actinomyces* infected lung tissues were infiltrated and showed stronger cANGPTL4 staining than normal healthy lung tissues. Blood vessels also showed more cANGPTL4 staining together with the surrounding tissues.

Clinical Sample Analysis (with Bacterial Pneumonia) Reveals Similar cAngptl4 Upregulation Pattern as in Influenza Pneumonia (FIG. 5)

Clinical samples were collected from patients. The lung tissues were identified by pathologist as either healthy lung tissue or pneumonia lung tissue. The source of pneumonia has been identified by clinicians. Formalin-fixed-paraffin-embedded clinical samples for both normal healthy lung tissue and bacterial infected lung tissue with pneumonia were sectioned and stained for cAngptl4 detection. In normal healthy lung tissue, cAngptl4 staining detected minimum cAngptl4 expression in the alveolar space, and the cAngptl4 expression was mainly found on endothelium. In contrast, in *actinomyces* infected lung tissue, cAngptl4 staining detected much up-regulated cAngptl4 expression in alveolar space, and the expression of cAngptl4 is not limited to endothelium, confirming the pattern found in animal model with influenza infection.

Example 6

Figure 6:
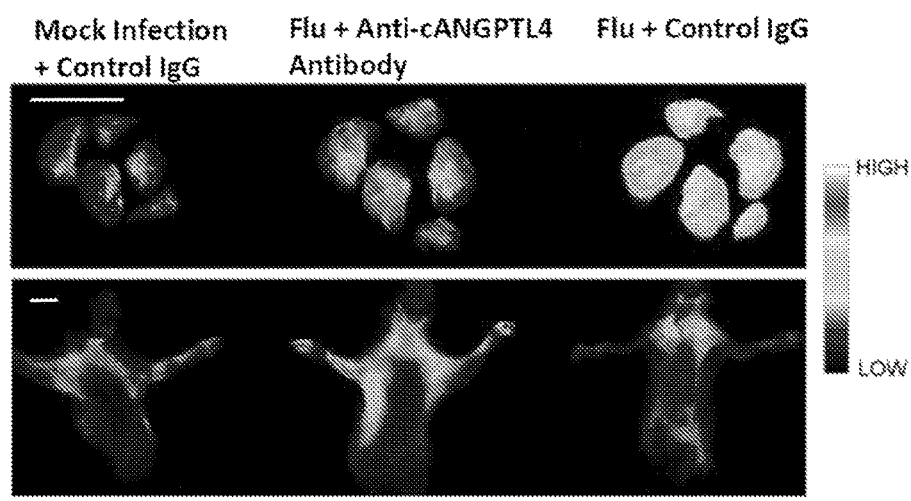
FIG. 6: Anti-cANGPTL4 Antibody Treatment Shows Significant Effect in Reducing Blood Vessel Permeability and Pneumonia Severity. In vivo imaging showing reduced blood vessel leakage for infected mice with antibody treatment. The PEG contrast agent will accumulate inside the organ where the blood vessel leaks. The signal strength indicates the blood vessel leakage. For mock infected mice, minimum signal was detected inside the lung, showing minimal blood vessel leakage under healthy condition of the lung. Infected mice with only control IgG injection showed high level of signal, indicating significantly increased blood vessel leakage with influenza infection and inflammation. For mice infected with influenza and treated with anti-cANGPTL4 antibody, the significantly decreased signal indicates significant reduction in blood vessel leakage with the anti-cANGPTL4 antibody treatment. Scale bars represent 1.5 cm length.

Anti-cANGPTL4 Antibody Treatment Shows Significant Effect in Reducing Blood Vessel Permeability and Pneumonia Severity. (FIG. 6)

In vivo imaging showing reduced blood vessel leakage for infected mice with antibody treatment. The PEG contrast agent will accumulate inside the organ where the blood vessel leaks. The signal strength indicates the blood vessel leakage. For mock infected mice, minimum signal was detected inside the lung, showing minimal blood vessel leakage under healthy condition of the lung. Infected mice with only control IgG injection showed high level of signal, indicating significantly increased blood vessel leakage with influenza infection and inflammation. For mice infected with influenza and treated with anti-cANGPTL4 antibody, the significantly decreased signal indicates significant reduction in blood vessel leakage with the anti-cANGPTL4 antibody treatment.

Example 7

Figure 7:
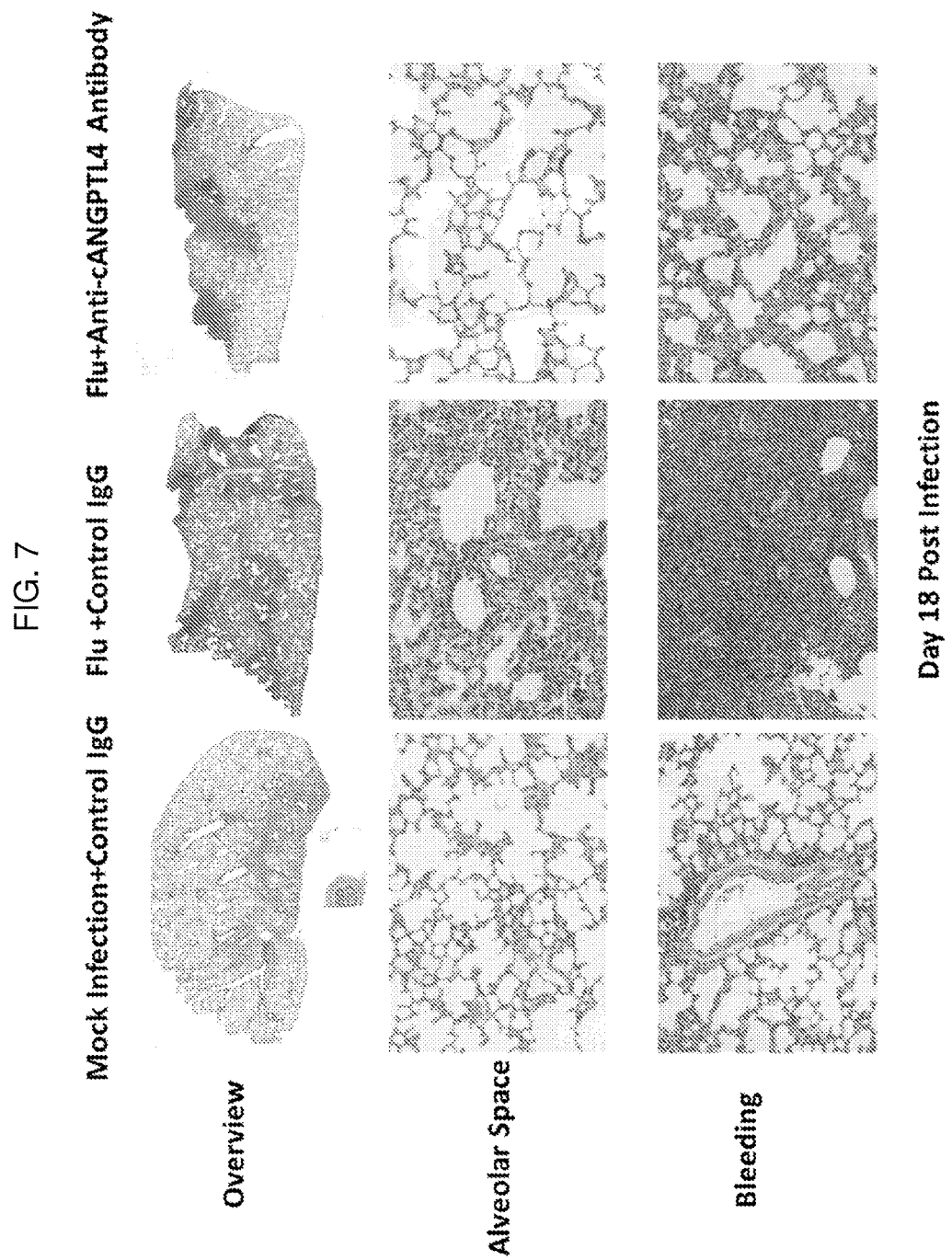
FIG. 7: Treatment using cAngptl4 Antibody Improves Lung Tissue Recovery after Influenza Infection. Mice were either 1) mock infected with PBS, injected with control IgG that does not bind to any specific antigen, 2) infected with PR8, injected with control IgG, or 3) infected with PR8, injected with monoclonal anti-cAngptl4 antibody. All the injection was carried out daily during day 13 to 17 post infection and lung were harvested at day 18. Each picture is representative of 5 mice for each experimental group. H&E staining showed the extent of tissue damage. Infected mice (group 3) that received anti-cAngptl4 antibody showed less tissue damage when compared to mice in group 1 and 2. The alveolar space of the treated group 3 also shows improvement than the non-treated group 2. The recovered structure is indistinguishable from non-infected mice (group 1). The cAngptl4 antibody treatment (group 3) also greatly reduced the bleeding in influenza-infected mice.

Treatment using cAngptl4 Antibody Improves Lung Tissue Recovery after Influenza Infection (FIG. 7)

Mice were either 1) mock infected with PBS, injected with control IgG that does not bind to any specific antigen, 2) infected with PR8, injected with control IgG, or 3) infected with PR8, injected with monoclonal anti-cAngptl4 antibody. All the injection was carried out daily during day 13 to 17 post infection and lung were harvested at day 18. Infected mice (group 3) that received anti-cAngptl4 antibody showed less tissue damage when compared to mice in group 1 and 2. The alveolar space of the treated group 3 also shows improvement when compared to the non-treated group 2. The recovered structure is indistinguishable from non-infected mice (group 1). The cAngptl4 antibody treatment (group 3) also greatly reduced the bleeding in influenza-infected mice. The better tissue integrity as a result of cAngptl4 antibody treatment after influenza infection indicates better lung function for the experimental animals.

Example 8

Figure 8:
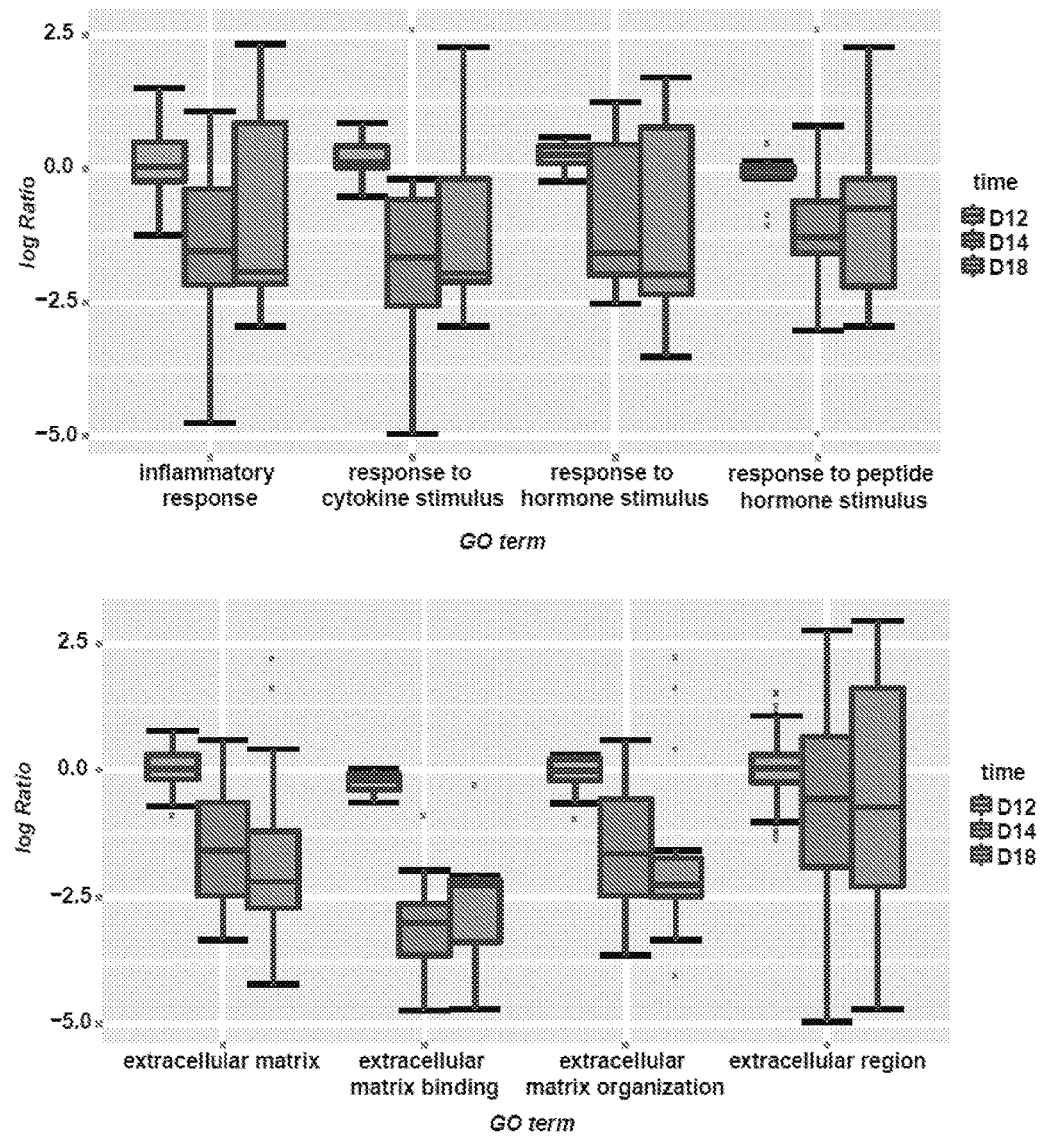
FIG. 8: Microarray data showing antibody treatment reduces inflammatory responses and extracellular matrix activities.

Microarray Data Showing Antibody Treatment Reduces Inflammatory Responses and Extracellular Matrix Activities. (FIG. 8)

Microarray data showed reduction of inflammatory responses, cytokine stimulus, hormone stimulus and peptide hormone stimulus by the antibody treatment, which reflects the effect following the neutralization of cANGPTL4 with antibody injection. Moreover, inhibition on extracellular matrix related activities was also observed, indicating a reduced risk for lung fibrosis with antibody treatment.

Example 9

Tissue Differentiation and Regeneration were Enhanced in Anti-cANGPTL4 Antibody Treated Mouse Lung Samples Following Influenza Infection (FIG. 9)

(a) Staining with CC10 (Clara cell marker) and SPC (Type II alveolar epithelial cell marker) shows that in anti-cANGPTL4 antibody treated influenza infected mouse lung samples there is increased Clara cells differentiation into SPC positive cells compared with control IgG treated influenza infected mouse lung samples, which was shown as an important process that repairs damaged alveolar spaces [Zheng D, et al 2012]. (b) A significant increase effect in this differentiation process in anti-cANGPTL4 antibody treated influenza infected mouse sample was shown compared with control IgG treated influenza infected mouse sample by calculating the amount of differentiated bronchioles in each lung section from all the five mouse samples in each experimental group. (c) Lung sections with anti-cANGPTL4 treatment and influenza infection also showed better PDPN regeneration in infiltrated lung regions than control IgG-treated influenza infected lung sections, indicating better tissue regeneration in anti-cANGPTL4 treated mice following influenza infection.

REFERENCES

Regeneration of Alveolar Type I and II Cells from Scgb1a1-Expressing Cells following Severe Pulmonary Damage Induced by Bleomycin and Influenza. Zheng D, Limmon G V, Yin L, Leung N H N, Yu H, et al. (2012) PLoS ONE 7(10): e48451. doi: 10. 1371/journal. pone.0048451);

Angiopoietin-like 4: a decade of research. Zhu P, Goh Y Y, Chin H F A, Kersten S and Tan N S. Biosci. Rep. 32/211-219, 2012.

Angptl4 protects against severe pro-inflammatory effects of dietary saturated fat by inhibiting fatty acid uptake into mesenteric lymph node macrophages. Lichtenstein, L., Mattijssen, F., de Wit N.J., Georgiadi, A., Hooiveld, G. J., can der Meer, R., He, Y., Qi, L., Koster, A., Tamsma, J. T., Tan, N. S., Müller, M. and Kersten, S. Cell Metabolism. 12(6): 580-592, 2010.

Angiopoietin-like 4 Protein Elevates the Prosurvival Intracellular O2-:H2O2 Ratio and Confers Anoikis Resistance to Tumors. Zhu P, et al. Cancer Cell 19, 401-415, Mar. 15, 2011.

Pathogenesis of influenza virus-induced pneumonia—Involvement of both nitric oxide and oxygen radicals. Akaike T, Noguchi Y, Ijiri S, Setguchi K, Suga M, Zheng Y M, Dietzschold B, Maeda H. Proc Natl Acad Sci USA 93:2448-2453, 1996.

Time-Dependent Airway Epithelial and Inflammatory Cell Responses Induced by Influenza Virus A/PR/8/34 in C57BL/6 Mice. Buchweitz J P, Harkema J R, and Kaminski N E. Toxicologic Pathology, 35:424-435, 2007.

The invention claimed is:

1. A method to monitor an acute inflammation of the lung in response to a microbial infection in a subject, comprising:
   i) providing an isolated biological sample from the subject, wherein the sample is a lung tissue sample or bronchial lavage fluid sample;
   ii) forming a preparation comprising said sample and an antibody that specifically binds an amino acid sequence set forth as SEQ ID NO: 3 or SEQ ID NO: 4 in a carboxyl-terminal fragment of angiopoietin-related protein 4 (cANGPTL4) in a polypeptide in said sample to form an antibody/polypeptide complex;
   iii) detecting the complex in the sample to determine the level of expression of the polypeptide in said sample; and
   iv) comparing the level of expression of said polypeptide with a normal matched control;
   wherein an increase in the level of expression of said polypeptide compared to the control identifies the subject as having acute inflammation of the lung in response to a microbial infection.

2. The method according to claim 1, wherein the antibody comprises a light chain variable region comprising light chain complementarity determining regions including the amino acid sequences KASQSVDYDGDSYLN [SEQ ID NO: 16], TASNLES [SEQ ID NO: 18], and QQSNEDPW [SEQ ID NO: 20] and a heavy chain variable region comprising heavy chain complementarity determining regions including the amino acid sequences TSGMGVG [SEQ ID NO: 22], HIWWDDDKYYNPSLK [SEQ ID NO: 24], and KDYGSSYDY [SEQ ID NO: 26].

3. The method according to claim 2, wherein the heavy chain variable region and the light chain variable region comprise amino acid sequences set forth as SEQ ID NO: 14 and SEQ ID NO: 13, respectively.

4. The method according to claim 1, further comprising: administering a treatment regimen to the subject, wherein said treatment regimen comprises administration of an antibody that specifically binds to an amino acid sequence set forth as SEQ ID NO: 3 or SEQ ID NO: 4 in a cANGPTL4 to the subject to treat the acute inflammation of the lung in response to a microbial infection in the subject, wherein the antibody inhibits activity of cANGPTL4.

5. The method according to claim 4, further comprising monitoring the acute inflammation of the lung in response to the microbial infection in the subject at or near the end of the treatment regimen to determine the effect of said treatment on the acute inflammation of the lung in the subject, wherein a reduction in expression of the polypeptide at or near the end of the treatment regimen indicates a reduction in microbial infection-induced acute lung inflammation.

6. The method of claim 1, wherein the method is repeated at or near the end of a treatment regimen for the microbial infection in the subject to determine the effect of the treatment on the acute inflammation of the lung in the subject, wherein a reduction in expression of the polypeptide at or near the end of the treatment regimen indicates a reduction in microbial infection-induced acute lung inflammation.

7. The method according to claim 1, further comprising administering a treatment regimen to the subject identified as having acute inflammation of the lung, wherein said treatment regimen comprises administration of a pharmaceutical composition comprising an anti-inflammatory agent or antibiotic.

* * * * *